United States Patent [19]

Neville, Jr. et al.

[11] Patent Number: 5,066,490

[45] Date of Patent: Nov. 19, 1991

[54] PROTEIN CROSSLINKING REAGENTS CLEAVABLE WITHIN ACIDIFIED INTRACELLULAR VESICLES

[75] Inventors: David M. Neville, Jr., Bethesda; Kasturi Srinivasachar, Rockville, both of Md.

[73] Assignee: The United States of America as represented by the Secretary of the Department of Health & Human Services, Washington, D.C.

[21] Appl. No.: 204,163

[22] Filed: Jun. 1, 1988

[51] Int. Cl.[5] ..................... A61K 39/44; A61K 37/48; C07K 17/02

[52] U.S. Cl. ................................ 424/85.91; 424/94.1; 530/345; 530/389; 530/391; 530/395; 530/397; 530/399; 530/409; 530/410; 435/188; 514/21; 548/407; 548/409

[58] Field of Search ............... 530/391, 389, 395, 399, 530/409, 410, 397, 345; 424/85.91, 94.1; 548/407, 521; 435/188; 514/21

[56] References Cited

U.S. PATENT DOCUMENTS

| | | | |
|---|---|---|---|
| 3,786,090 | 1/1974 | Hussain | 260/562 A |
| 4,150,033 | 4/1979 | Kitagawa | 260/326.26 |
| 4,356,117 | 10/1982 | Neville, Jr. et al. | 260/112 R |
| 4,359,457 | 11/1982 | Neville, Jr. et al. | 424/85.91 |
| 4,440,747 | 4/1984 | Neville, Jr. et al. | 424/85.91 |
| 4,500,637 | 2/1985 | Neville, Jr. et al. | 435/2 |
| 4,520,011 | 5/1985 | Neville, Jr. et al. | 424/85.91 |
| 4,520,226 | 5/1985 | Neville, Jr. et al. | 424/85.91 |
| 4,542,225 | 9/1985 | Blattler et al. | 548/473 |
| 4,618,492 | 10/1986 | Blattler et al. | 424/85.91 |

OTHER PUBLICATIONS

Neville, Jr. et al. (1989) J. Biol. Chem. 264:14653-14661.
Srinivasachar et al. (1989) Biochemistry 28:2501-2509.
Wang et al., *Isr. J. Chem.* 12: 375-378, 1974.
Lutter et al., *FEBS* 48: 288-292, 1974.
Neville, *CRC Crit. Revs. Ther. Drug Carrier Syst.* 2: 329-352, 1986.
Lambert et al., *J. Mol. Biol.* 149: 451-476, 1981.
Carlsson et al., *Biochem. J.* 173: 723-737, 1978.
Vitetta et al., *Science* 219: 644-650, 1983.
Edwards, *Pharmacol. Ther.* 23: 147-177, 1983.
Ramakrishnan et al., *Cancer Research* 44: 1398-1404, 1984.
Ritz et al., *Nature* 283: 583-585, 1980.
Stirpe et al., *J. Biol. Chem.* 255: 6947-6953, 1980.
Barbieri et al., *Biochem. J.* 203: 55-59, 1982.
Abuchowski et al., *J. Biol. Chem.* 252: 3582-3586, 1977.
Dixon et al., *Biochem. J.* 109: 312-314, 1968.
Cordes et al., *Chem. Rev.* 74: 581-603, 1974.
Heller et al., *Polym. Eng. Sci.* 21: 727, 1981.
Hussain et al., *J. Pharm. Sci.* 67: 546, 1978.
Greenfield et al., *Science* 238: 536-539, 1987.
King et al., *Nature*, 253: 420-423, 1975.

*Primary Examiner*—Jeffrey E. Russel
*Assistant Examiner*—Kay Kim
*Attorney, Agent, or Firm*—Birch, Stewart, Kolasch & Birch

[57] ABSTRACT

Crosslinking reagents for amino group-containing compounds are provided, which crosslinkers can be cleaved under mildly acidic conditions. The crosslinkers can be used to crosslink biologically active substances to be delivered to the cells, wherein the crosslinker will be cleaved in the mildly acidic conditions within the cell.

21 Claims, 11 Drawing Sheets

1

2

3

4

PROTEIN CROSSLINKING REAGENTS CLEAVABLE WITHIN ACIDIFIED INTRACELLULAR VESICLES

FIELD OF THE INVENTION

The present invention relates to protein crosslinking reagents which can be cleaved under acidic conditions. The crosslinked products so formed can be used to deposit within a cell a non-crosslinked protein or other molecule which is transported to the cell as a cross-linked protein utilizing receptor-mediated endocytosis; to construct therapeutic prodrugs; and to reversibly couple proteins to matrices for synthetic and chromatographic purposes.

BACKGROUND OF THE INVENTION

There are numerous situations wherein it may be desirable to control the release of amino-group-containing substances to liquid media. For example, it may be desirable to control the release of an amino-group-containing drug or cytotoxin to a cell population or specific members of a cell population. It may also be desirable to control the cleavage of various cross-linked proteins or peptides, for example, in analyzing the spatial relationships in a complex of large amino-group-containing molecules such as peptides or proteins.

One specific situation in which controlled release is desirable is in delivering a biologically active compound through the cell membrane to inner cell structures, for example, where the compound has a low or reduced effect if trapped in the medium outside the cell membrane but is more potent once released inside the cell.

It is also desirable to be able to deliver biologically active compounds to selected cells in a heterogeneous cell population. For example, in treating diseased or infected cells such as virus-infected cells or transformed or malignant cells, it is desirable to deliver cytotoxins anti-viral agents or growth regulating factors to the diseased or malignant cells but not to normal cells.

One approach disclosed for targeting biologically active compounds to malignant cells uses an antibody-toxin conjugate. The antibody is specific for malignant cells and delivers the toxin to them. To be effective, these systems should deliver the toxin with high selectivity to the target cells without unnecessarily reducing the effectiveness of the active substance. These problems are particularly important where the goal is destruction of infected or diseased cells in vivo without harming normal cells.

A variety of protein crosslinking reagents are commercially available. Those crosslinkers in widest use are heterobifunctional reagents using maleimide and N-hydroxysuccinimide esters. Specific coupling of two proteins via a non-cleavable thioether bond is achieved by introducing an SH group into one of the proteins, as disclosed by Kitagawa, U.S. Pat. No. 4,150,033. Commercially available cleavable crosslinkers are limited to disulfide, carboxylic acid ester, and vic-glycol groupings requiring -SH reagents, strong nucleophiles, or periodate oxidation, which permanently modify many proteins, cf. Wang et al., *Isr. J. Chem.* 12:375-378, 1974; Lutter et al , *FEBS* 48 288-292, 1974.Disulfide reagents are only slowly cleaved within the cells.

It was found by Neville, *CRC Crit. Revs. Ther. Drug Carrier Syst.* 2:329-352, 1986, that the efficacy of holotoxin conjugates coupled via disulfide bonds is not superior to thioether crosslinking.

Additional cleavable bifunctional crosslinking reagents are known, including Lambert et al., *J. Mol. Biol.* 149: 451-476 (198I) and Wang et al., *Isr. J. Chem.* 12: 375-389 (1974) wherein are disclosed bifunctional crosslinking reagents containing a cleavable disulfide bond The reagents are used to characterize biochemical systems.

Carlsson et al., *Biochem. J.* 173: 723-737 (1978) disclose a procedure for forming disulfide bonds between two different proteins using the bifunctional reagent N-succinimidyl-3-(2-pyridyldithio)propionate.

More specifically, certain monoclonal antibodies, toxins, and conjugates thereof are known.

Vitetta et al, in *Science* 219: 644-650 (1983) and Edwards, *Pharmacol. Ther.* 23: 147-177 (1983) disclose disulfide-linked conjugates of toxins and monoclonal antibodies specific to cell-surface structures. These conjugates are used to target toxins toward specific cells having surface structures recognized by the antibodies.

Ramakrishnan et al., in *Cancer Research* 44: 1398-1404 (1984) disclose conjugating pokeweed antiviral protein (PAP) to anti-Thy 1.1, a monoclonal antibody. The conjugate is used to inhibit protein synthesis selectively in Thy 1.1-positive target leukemia cells. The linker used to form the conjugate is N-succinimidyl-3-(2-pyridyldithio)propionate. When the disulfide bond is cleaved, the free PAP toxin is produced.

Ritz et al., *Nature* 283: 583-585 (1980) disclose a monoclonal antibody (J5) that is specific for common acute lymphoblastic leukemia antigen.

Stirpe et al. , *J. Biol Chem.* 255: 6947-6953 (1980) disclose a method for preparing gelonin, a protein cytotoxin.

Barbieri et al., *Biochem. J.* 203: 55-59 (1982) disclose the purification and partial characterization of an antiviral protein known as pokeweed antiviral proteins ("PAP-S").

Neville et al., U.S. Pat. No. 4,359,457, disclose a conjugate of anti-Thy 1.2 monoclonal antibody and ricin used as a tumor suppressive composition against lymphoma. The linking agent used is m-maleimidobenzoyl-N-hydroxysuccinimide.

The above-described approaches either depend on the toxicity of an antibody-toxin conjugate, or they depend on disulfide bond cleavage, a phenomenon that may be difficult to control temporally and spatially to avoid release of the toxin before delivery to the targeted cells.

An acid cleavable protein crosslinker has been described based on a citraconic anhydride group by Blattler et al., U.S. Pat. Nos. 4,542,225, 4,618,492. Deficiencies in this scheme include the fact that the hydrolysis rate is not linearly correlated with the hydrogen ion concentration (a 30-fold change in hydrolysis for a 600-fold change in $[H+]$, there is a potential for forming an irreversible crosslink through Michael type additions of cellular SH groups to the double bond, there is a failure to demonstrate significant hydrolysis of crosslinked product at the low end of the intravesicle pH (5.4), i.e., <25% hydrolysis at pH 5.5 in 10 hours, and there is a failure to demonstrate efficacy over non-cleavable crosslinkers in a system involving protein uptake either by tissue culture or in vivo, as well as a lengthy synthetic sequence.

Kirby et al. , *Proc. Biochem. Soc. Symp.* 31: 99-103 (1970) disclose that maleic acid amides are rapidly hydrolyzed below pH 3, and that substitution of maleamic acid increases that rate, with a t-butyl substituent providing the largest increase and a methyl substituent the smallest.

Dixon et al., *Biochem. J.* 109: 312-314 (1968) disclose reversible blocking of amino groups using 2-methylmaleic (citraconic) anhydride as a blocking agent. The amine bond between the citraconyl residue and a lysine residue of insulin was not cleaved at pH 6.5; when the pH was lowered to 3.5 at 20° C. overnight, there was total release of the blocking group, leaving the insulin unchanged.

The concept of a prodrug is not new, and has been described by Albert in *Nature* 182:421-423, 1975. The acid catalyzed hydrolytic properties of orthoesters, acetals, and ketals are well described, particularly by Cordes et al in *Chem. Rev.* 74 581-603, 1974, and have been used to achieve prodrugs in the slow release of subcutaneously implanted steroid contraceptives from a solid orthoester polymer matrix, Heller et al., *Polym. Eng. Sci.* 21: 727, 1981, and in the gastric release of acetaminophen from a more pleasant tasting acetal prodrug, Hussain, U.S. Pat. No. 3,786,090. The log of the hydrolytic rate constant of this drug was found to be linear with pH over the range of pH 2-6, Hussain et al., *J. Pharm. Sci.* 67: 546-546 1978.

The extension of the above basic chemistry to a protein crosslinker capable of release within intracellular compartments was not trivial. The starting materials for orthoester synthesis, ketene acetals, are notoriously difficult to work with because of cationic polymerization side reactions. Synthetic routes could not use strong acid conditions, and the desired maleimide functionality limited many approaches, such as orthoesters via the Pinner synthesis. These limitations were particularly bothersome for the synthesis of the heterobifunctional reagents which classically employ harsh conditions Neville et al., in U.S. Pat. Nos. 4,356,117; 4,359,457; 4,440,747; 4,500,637; 4,520,011; and 4,520,26; elucidate the concepts and utility of constructing monoclonal antibody-protein toxin conjugates (immunotoxins) directed at specific unwanted target cells. Holo-ricin based immunotoxins have greater efficacy than ricin A chain immunotoxins. The enhanced efficiency of such holotoxin conjugates over those constructed with toxin A-chains has been documented. The discrimination between target and nontarget cell was maintained by reversibly blocking the ricin toxin B chain binding site with lactose, since this site has been shown to be essential for full immunotoxin efficacy, as lactose is extruded from the cell following endocytosis. The ricin binding site is required for efficient membrane translocation of ricin within the cell, and lactose blocks ricin binding outside the cell but not inside the cell because lactose is actively transported out of the cell. However, such conjugates reversibly blocked with lactose have limited in vivo efficacy, since high concentrations of lactose cannot be maintained in vivo without untoward effects.

Acid cleavable crosslinkers permit reversible blockade of the ricin binding sites by crosslinking asialoglycoproteins, and asialoglycopeptides, and mannose binding proteins to these sites which can dissociate in the acidified vesicle. In addition, the translocation functions of mutant diphtheria toxins such as CRM 103 and CRM 107, which are partially blocked by coupling to monoclonal antibodies with conventional crosslinkers (Greenfield et al. *Science* 238 536-539, 1987) can be uncoupled within the cell using a cleavable crosslinker. Since these toxin mutants, which are binding domain mutants, have reduced non-target cell specificity to begin with, they should be suitable for in vivo use Immunotoxins of CRM 103 and CRM 107 constructed with acid cleavable crosslinkers should provide an extra I to 2 logs increase in efficacy over the conventional crosslinkers.

Polyethylene glycol (PEG) has been conjugated to proteins by a variety of procedures to block certain functional domains in vivo, Aubuchowski et al., *J. Biol. Chem.* 252: 3582-3586, 1976, These PEG conjugates can be used to administer an enzyme protein missing from the body in order to correct an enzyme deficiency disease. PEG coupling can minimize two problems, namely, rapid clearance of the unmodified protein from the vascular system, either antibody or extra antibody mediated, and the formation of antibodies to the foreign protein. Rapid clearance and antigenic stimulation are also problems concerning the in vivo use of immunotoxins. However, PEG, like antibody coupling, also interferes with toxin translocation.

SUMMARY OF THE INVENTION

It is an object of the present invention to overcome the above-mentioned deficiencies in the prior art.

It is another object of the present invention to provide crosslinking reagents for proteins which can be cleaved under mild acidic conditions.

It is still another object of the present invention to provide a method for synthesizing crosslinking agents.

It is a further object of the present invention to provide a method to deposit efficiently within a cell a non-crosslinked protein or other molecule which has been previously transported into the cell as a crosslinked protein or other molecule, using receptor-mediated endocytosis.

It is yet another object of the present invention to provide therapeutic prodrugs.

It is yet a further object of the present invention to reversibly couple proteins to matrices for synthetic and chromatographic purposes.

It is still a further object of the present invention to provide compositions which can be used in the treatment of cancer.

It is still another object of the present invention to provide compositions which can be used in the treatment of acquired immune deficiency syndrome (AIDS).

It is still a further object of the present invention to provide compositions which can break the infectious cycles of viruses.

Yet another object of the present invention is to provide compositions which can be used to kill T cells.

According to the present invention, compounds are provided which permit the crosslinking of two amino and/or sulfhydryl group containing substances at pH $>7$, and which will release these substances under mildly acidic conditions with little or no attenuation of activity.

The preferred biologically active substances to be delivered to the cells by the method of the present invention is a protein or a peptide or a drug or an enzyme or a nucleic acid. Most preferably, the active substance is a cell toxin to be delivered to selected cells, such as ricin, diphtheria toxin, abrin, and other ribosomal-inactivating proteins or elongation factor 2 inactivating proteins Peptide toxins are preferred because they are readily bound to the reagent and because they are extremely potent toxins which inhibit cell protein synthesis when present inside the cell in extremely minute quantities. Other amino-group-containing cytotoxins which are not peptides are also within the scope of the invention, such as melphalan, bleomycin, adriamycin, and daunomycin.

The conjugates are delivered to selected cells by binding partners to cell-surface features. The preferred binding partners are antibodies to cell surface antigens Particularly preferred are monoclonal antibodies to cell surface antigens specific to diseased, infected, transformed, or malignant cells, but not to normal cells. Particularly, but not exclusively, they are antibodies that are taken up by the cells. It is not necessary that non-target cells lack the specific antigen entirely, as long as the antigen is not present in sufficient numbers on those cells to permit significant uptake of the active substance by the cells.

Examples of such antibodies are antibodies to melanoma surface antigens and the antibodies to surface antigens found on T-cells and T-cell lymphomas, such as CD-3, CD-4, CD-5, CD-11, and CD-12.

Other binding partners that can be used include non-antibody cell membrane transport agents such as transferrin and protein hormones or growth factors such as insulin.

The hydrolytic rates are such that these crosslinkers are cleaved within minutes or hours at the pH of acidified cellular vesicles, pH 5.4, yet are 100 times more stable at the intravascular pH of 7.4, and 1000 times more stable at a storage pH of 8.4.

The essential points of the present invention are that the cellular component causing cleavage is not appreciably present in the serum, the cellular component causing cleavage is present within a compartment to which the immunotoxin is routed by the targeting moiety, and the intracellular cleavage is sufficiently rapid to restore substantially full activity of the active molecule.

The crosslinking agents of the present invention comprise the unit:

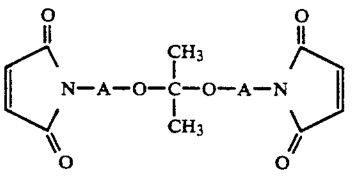

wherein A is bridge unit which is unreactive with the protein or other molecules to be crosslinked and has functionalities which are compatible with maleimide groups. The bridge may include peptide chains, aromatic substituents, and the like. A is preferably $(CH_2)_n$, where n is an integer of from 1 to 8. Methyl groups $(CH_3)$ are the preferred central carbon substituent but other groups having similar electron donating capacity such as $C_2$–$C_9$ alkyl, phenyl, or substituted phenyl, can be used.

In a second aspect of the invention, a heterobifunctional acid cleavable crosslinker is provided which is suitable for linking an amino group containing substance to a sulfhydryl group on a second compound. This reagent has the general formula:

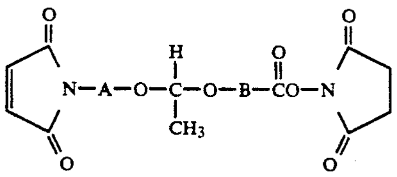

wherein A and B are bridge units, A being the same as defined above, and B is:

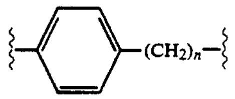

where n is an integer of at least 1.

In a third aspect of the present invention, methods are provided for synthesizing the crosslinking reagents of the present invention either by ketal exchange reactions between commercially available ketals and alcohols containing a maleimide functionality, or the acid catalyzed addition of phenols derivatized with an N-hydroxysuccinimide ester grouping to vinyl ethers bearing a maleimide moiety.

In a fourth aspect of the present invention, homobifunctional crosslinkers are provided in which the acid labile moiety is an orthoester function and which contain the maleimide group for reaction with sulfhydryl containing compounds. These crosslinkers have the general structure:

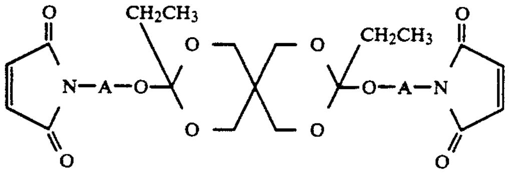

wherein A is a bridge unit as defined above.

The fifth aspect of the present invention features a method for the synthesis of the orthoester class of crosslinkers by the reaction of an appropriate alcohol with a bis-ketene acetal. FIGS. 1, 2, and 3 illustrate in flow diagram form the synthesis of ketal, acetal, and the orthoester class of crosslinkers.

DETAILED DESCRIPTION OF THE INVENTION

The cleavable crosslinkers of the present invention have three major utilities:

1. The crosslinkers can be used to efficiently deposit within a cell a non-crosslinked protein or other macromolecule which is transported into the cell as a crosslinked protein utilizing receptor-mediated endocytosis dictated by one of the crosslinked proteins. An example of this is the efficient loading of ricin and diphtheria toxin into cells via an anti-CD5 monoclonal antibody-toxin complex (immunotoxin), which can be used to kill T cells. Immunotoxins constructed with these cleavable crosslinkers are 10-50 times more toxic toward target cells than the best conventional non-cleavable crosslinkers.

2. The crosslinkers of the present invention can be used to construct therapeutic prodrugs. A specific functionality of an administered therapeutic protein or an agent attached to a protein is blocked while outside of the target cell, but is unblocked within the target cell. This achieves a higher therapeutic ratio by reversibly altering functionalities which direct proteins to certain cells or organs. Lifetime within the vascular compartment, clearance by preexisting antibodies, and antigenic stimulation can also be modified in this way. One example of the reversible blocking of a protein functionality is the blocking and unblocking of protein toxin binding sites which is correlated with cellular toxicity.

3. Crosslinkers cleavable under non-denaturing conditions are valuable research tools to reversibly couple proteins and other compounds having amino and/or sulfhydryl groups to matrices for synthetic and chromatographic purposes, to assess neighbor-neighbor interactions, to follow the passage of macromolecules through intracellular compartments, some of which are acidified, and to assess the inhibitory effects of molecular derivatization procedures.

All of the crosslinkers of the present invention, with the exception of compound 2, are homobifunctional reagents containing the maleimide functionality. Maleimide groups are highly specific for sulfhydryl groups which can be readily generated on a protein or other amino group containing substance by methods well known in the art. The heterobifunctional reagent 2 forms a crosslink between an amino group on one component and a sulfhydryl group on another component.

With respect to the present invention, the nature of the crosslinker joining the two protein molecules is well defined. The crosslinker should be easy to synthesize in large amounts, and should have good stability for long-term storage. The coupling reaction should take place under mild conditions which do not affect protein structure or activity. The crosslinked product should be reasonably stable during storage and should not be cleaved prematurely, i.e., the linkage should be inert at pH at least 7.4, but should be rapidly cleaved in the pH range or 5 to 6, releasing the individual proteins without attenuation of activity

Figure 1:
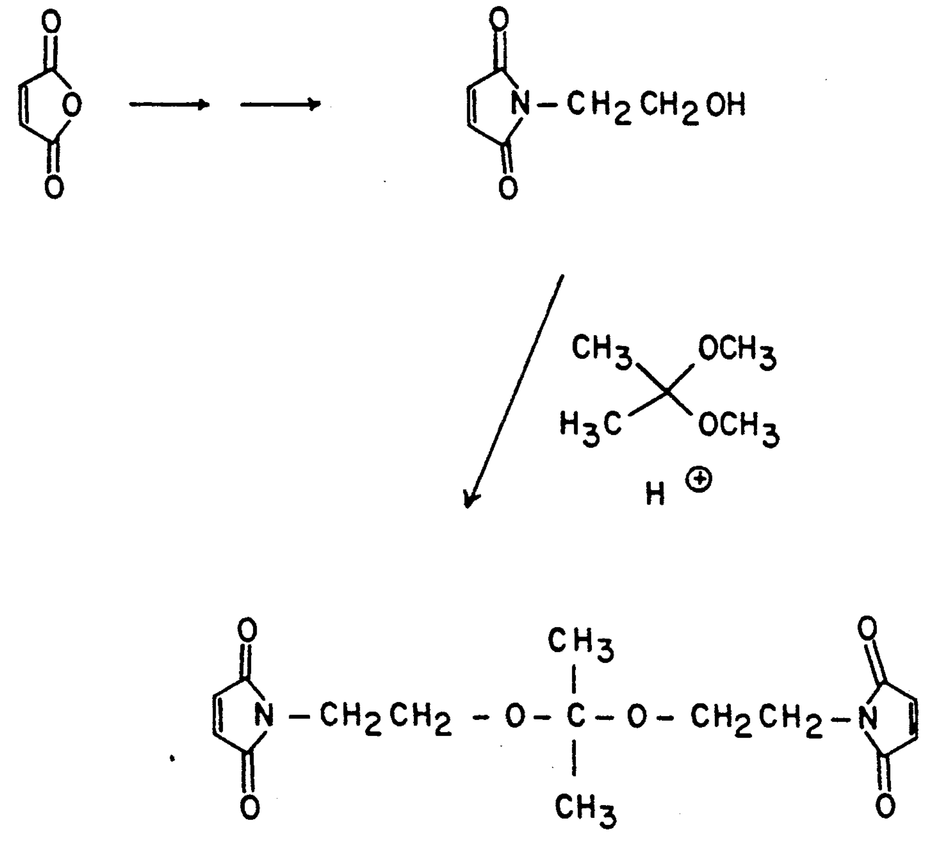
FIG. 1 shows the synthesis of crosslinker 1.

Synthesis of a Bis-maleimide Ketal Crosslinker (FIG. 1)

This synthesis involves a ketal exchange reaction between N-(2-hydroxyethyl) maleimide and 2,2-dimethoxypropane. The exchange is catalyzed by trace amounts of acids, e.g., p-toluenesulfonic acid.

N-(2-hydroxyethyl) maleimide was prepared according to the method of Kosower et al., *J. Med. Chem.* 14: 873–838, 1971. 141 mg of this material was suspended in 10 mL benzene, and 75 mg of 2,2-dimethoxypropane was added. The mixture was stirred at room temperature under an argon atmosphere and 0.25–0.5 mg p-toluenesulfonic acid was added as a catalyst. After the reaction mixture turned homogeneous, the solvent was distilled off and another 50 mg portion of 2,2-dimethoxypropane in 10 mL benzene was added. Stirring was continued at room temperature for an additional two hours. A few drops of pyridine were added to neutralize the acid. The solvents were distilled off, and 10 ml of benzene was added to the residue. The benzene soluble portion was decanted off and evaporated to dryness. The residue was crystallized from acetone-hexane to yield white, fluffy crystals, mp 124°–126°.

Crosslinker 5, similar to crosslinker 1 with one less $CH_2$ group in each bridge was prepared in a similar manner and isolated as a crystalline solid.

Figure 2:
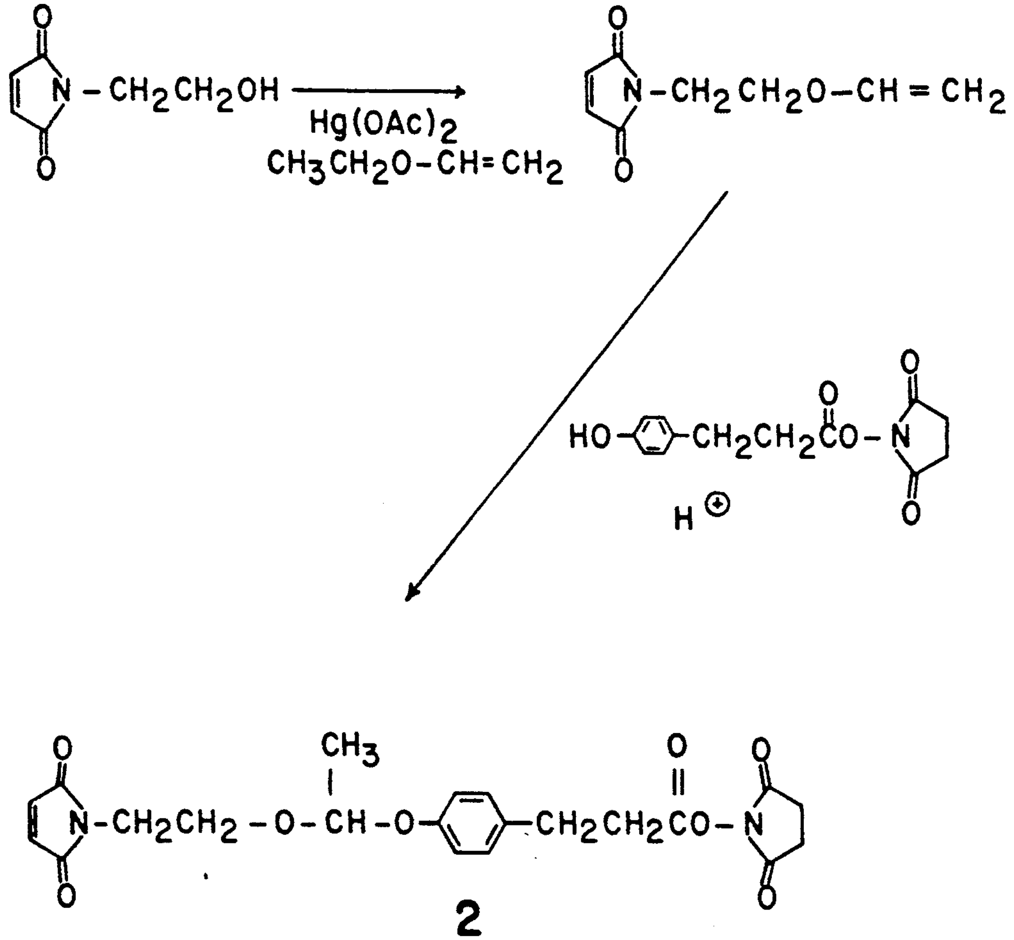
FIG. 2 shows the synthesis of heterobifunctional crosslinker 2.

Synthesis of a Heterobifunctional Acetal Crosslinker (FIG. 2)

This synthesis comprises adding a phenol derivatized with a N-hydroxysuccinimide ester functionality to a vinyl ether containing a maleimide group. The addition is acid catalyzed.

Preparation of 2-Maleimidoethyl vinyl ether

A quantity of 1.18 g of N-(2-hydroxyethyl)maleimide was suspended in 25 ml ethyl vinyl ether and refluxed with stirring under an argon atmosphere, 70 mg mercuric acetate was added, and the reaction was continued at reflux for 24 hours. After 24 hours, the reaction mixture was allowed to cool to room temperature, and 1.50 mg of anhydrous potassium carbonate was added. After stirring for a few more minutes, the mixture was filtered and the precipitate was washed thoroughly with ethyl acetate. The washings were combined with the filtrate and evaporated to dryness in vacuo to yield an oily residue. This oily residue was chromatographed over 50 grams of neutral alumina, activity III, using methylene chloride-hexane (1:1) for elution. The initial fractions were collected and combined to yield 200 mg of crude 2-maleimidoethyl vinyl ether. The product was suitable for use in the next step in preparation of the crosslinker, but for analytical purposes could be purified by re-chromatography over alumina or kugelrohr distillation.

Crosslinking Reagent

One hundred twenty mg of 3-(4-hydroxyphenyl)propionic acid-N-hydroxysuccinimide ester was dissolved in 10 mL of anhydrous ethyl acetate, and 200 mg of maleimidoethyl vinyl ether was added. The reaction mixture was stirred at room temperature under argon, and a solution of 0.5 mg of p-toluenesulfonic acid in 1 mL anhydrous ethyl acetate was added as a catalyst. After a reaction time of six hours, a few drops of pyridine were added to neutralize the acid, and the reaction mixture was evaporated to dryness to yield a viscous pale yellow oil. Hexane was added to this residue, and the mixture was refrigerated for several hours. The white solid which precipitated, 200 mg, was collected and washed with hexane. Crystallization from methylene chloride-hexane yielded white crystals, mp 134°-147°.

Figure 3:
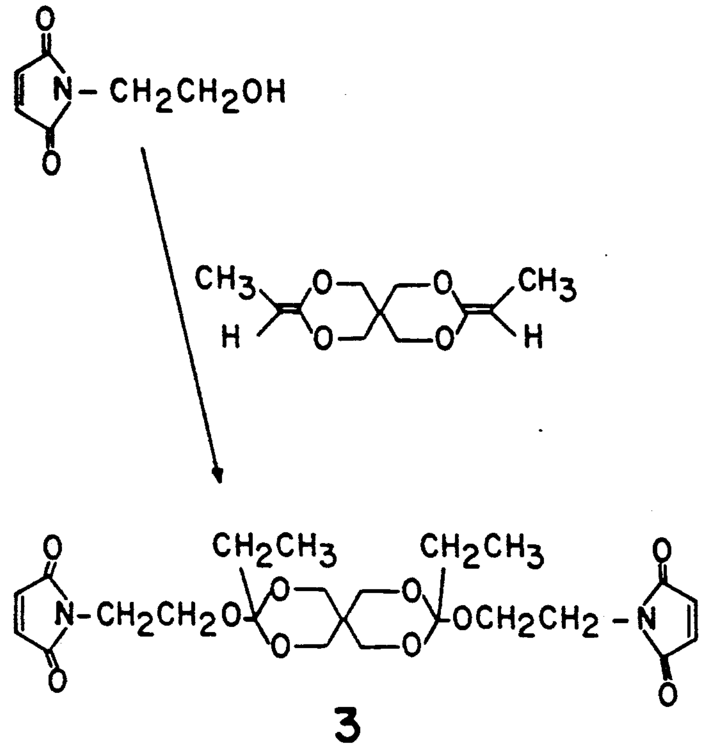
FIG. 3 shows the synthesis of orthoester crosslinkers 3 and 4.
Figure 3:
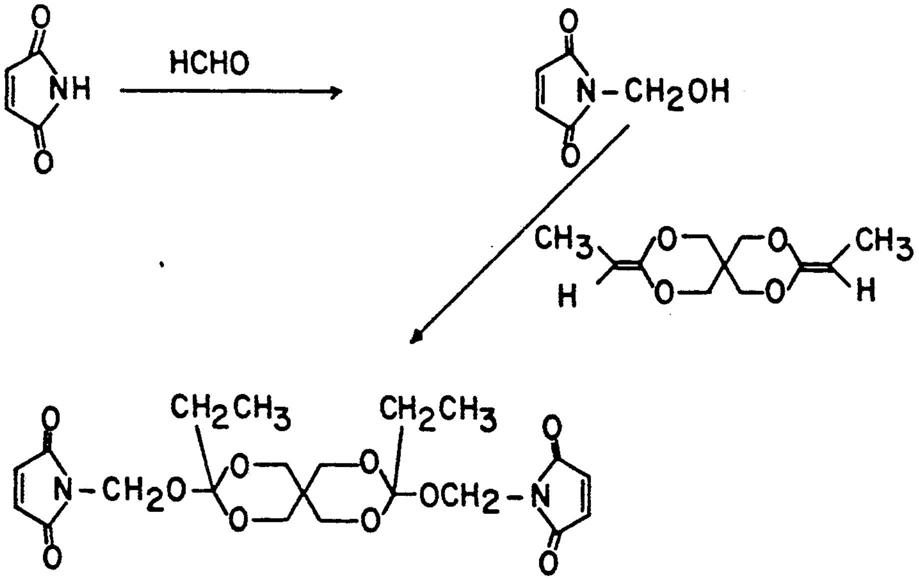

Synthesis of Orthoester Crosslinkers, FIG. 3

These crosslinkers are prepared by the addition of the appropriate alcohols ROH to the bisketene acetal

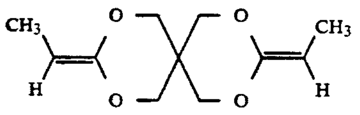

to give the orthoester of the general formula

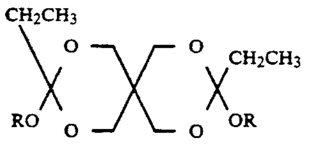

wherein R is $C_1$-$C_9$ alkyl.

The ketene acetal was prepared from the spiro compound

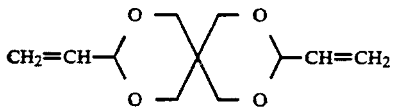

by a rearrangement induced by hexane solution of n-butyl lithium and ethylenediamine according to the procedure of Heller et al., 1986, submitted to *Macromolecular Synthesis.*

Two hundred fifty mg of N-hydroxymethyl maleimide, prepared from maleimide according to the method of Tawney et al. *J. Org. Chem.* 26: 15-21, 1961, was dissolved in 50 mL anhydrous ether, and the solution was treated with 220 mg of the ketene acetal. The homogeneous reaction mixture was stirred under an argon atmosphere at room temperature for one to two hours. A slight turbidity was observed, probably as a result of polymerization of a portion of the ketene acetal. The reaction mixture was filtered and concentrated to remove most but not all of the solvent. Hexane was added dropwise to initiate crystallization. The mixture was cooled in a refrigerator to complete crystallization. The white crystals were isolated by filtration and dried to yield 350 mg of the orthoester 4, mp 143°-146° (d).

An orthoester crosslinker 3 was prepared in the same manner, using N-hydroxyethyl maleimide in place of N-hydroxymethyl maleimide. The crosslinker in this example formed a colorless oil.

Other examples of acid cleavable crosslinkers are as follows:

Heterobifunctional acid cleavable ketal crosslinkers of the formula

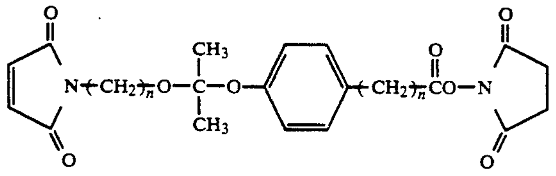

wherein $n \geq 1$

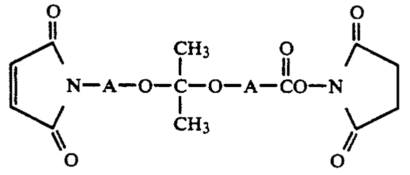

wherein A is bridge unit as described in p 10. Methyl groups ($CH_3$) are the preferred central carbon substituent but other groups having similar electron donating capacity such as $C_2$-$C_9$ alkyl, phenyl, or other substituted phenyl, can be used.

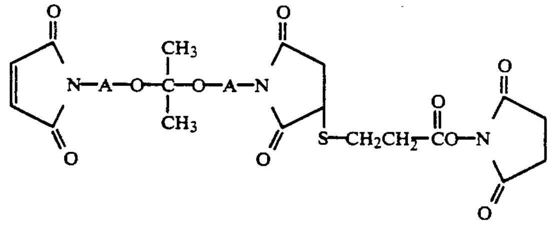

wherein A is as defined above.

Heterobifunctional acid cleavable acetal crosslinkers of the formula

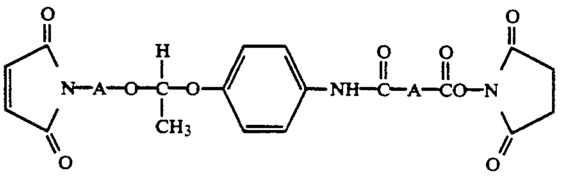

wherein A is as defined above.

Homobifunctional acid cleavable orthosester crosslinkers of the formula

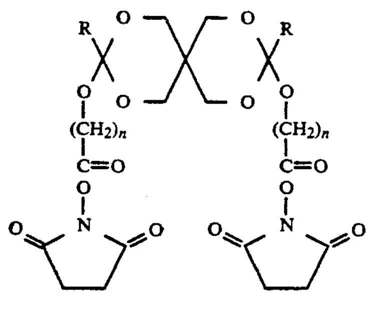

wherein R is alkyl of $C_1$-$C_8$ and $n \geqq 1$.

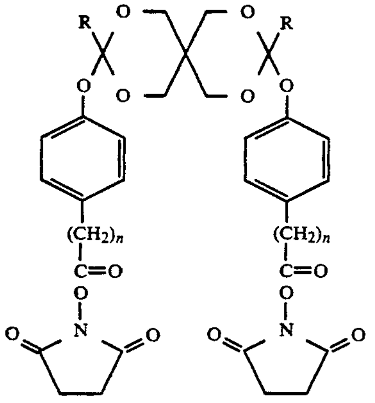

wherein R is alkyl of $C_1$-$C_8$ and $n \geqq 1$.

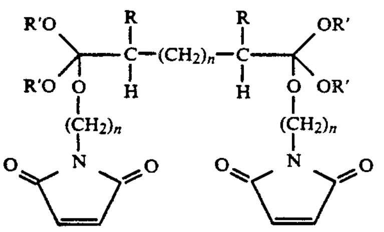

wherein $n \geqq 1$, R' is methyl or higher alkyl ($C_1$-$C_8$) and R is hydrogen or alkyl of $C_1$-$C_8$.

Advantages of Multiple Crosslinking Units

Figure 5:
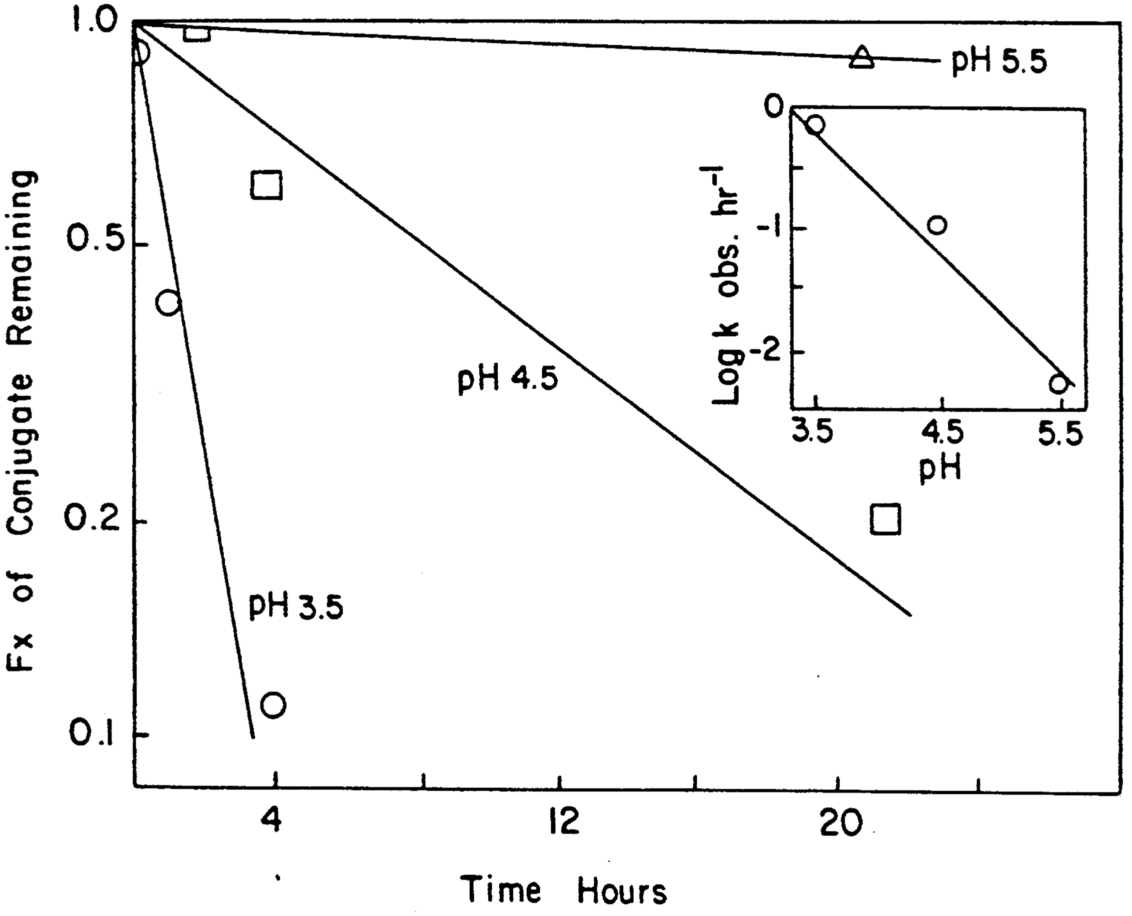
FIG. 5 shows the fractional loss of the immunotoxin T101-DT plotted on a log scale, followed by the appearance of free T101 antibody at pH 3.5, 4.5, and 5.5. The slope at each pH defines the observed first order rate constant of dissociation, k, and in the insert, log k is plotted vs pH, revealing a linear dependence, a characteristic of specific acid catalysis.

From the insert in FIG. 5, it can be seen that the slope of log $K_{obs}$ vs pH is 1. It would be advantageous to have $K_{obs}=k'[H]^x$ where the exponent x is at least 2. This would provide a 10,000-fold change or greater in the hydrolytic rate for a 100-fold change in [H+] between the vascular compartment and the endosomal compartment. This can be achieved by having the order of the reaction at least 2 with respect to [H+]. A typical chemical example is the dissociation of heavy metals from tetra acetate-acetic acid complexes. Using the present chemistry, two crosslinking units will provide a dependency on $K_{obs}=k'[H]^x$ where x approaches 2 at low values of the fraction of hydrolyzed material. The derivation comes from target theory and utilizes the Poisson formula, which predicts that, if the average number of random events in a single target is a, then the fraction of targets having exactly n events is $$\frac{e^{-a}a^n}{n!}$$

and the fraction of targets surviving, P, this is when n =0 is equal to $e^{-a}$.

This analysis can be extended to a multitarget model containing n targets (Hutchinson and Pollard in Mechanisms in Radiobiology Vol 1, General Principles [Errera and Forssbert, eds.] 1961, Academic Press, New York and London.) For two targets $P=e^{-a}(1+a)$ and for three targets, $$P = e^{-a}\left(1 + a + \frac{a^2}{2}\right)$$

The result for multi hit targets is that at low values of a, which may be equated to the product of an acid independent first order hydrolytic rate constant k', [H+] and time, P is increased. For example, for n=0, $P=e^{-a}$. At a=1. P=0.37. By going 100-fold higher in pH (time held constant), P increases to 0.99.

For two crosslinkers in parallel, the two hit model requires a =2.2 for P =0.37. However, for a=0.022 (100-fold change), P is now 0.99976, a significant increase. In practical terms, multiple crosslinks of sterically hindered toxin binding site are achieved in three ways:

1) Forming MAb-toxin conjugates with cleavable linkers in which the complex has the formula MAb-X-toxin-X-MAb. In practical terms, this is accomplished by doubling the thiol derivatization of the toxin two-fold, lowering the thiolation of the MAb by 0.5, and inputting reactants at a ratio of MAb to toxin to 1:1 to 4:1.

2) Synthesizing crosslinkers containing parallel cleavable bonds (X) placed between the protein coupling units Y and Z where B are bridging units, preferably $C_1$-$C_8$ alkyl,

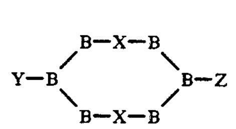

3) Using steric blocking groups such as polyethylene glycol where multiple polyethylene glycol units are attached to the toxin through the cleavable crosslinkers X MAb - X-Toxin-(X-PEG)n wherein n is greater than 2.

Another group of crosslinkers according to the present invention are acid reversible crosslinkers containing an azide group for photoinitiated crosslinking. A specific example of this type of crosslinker is

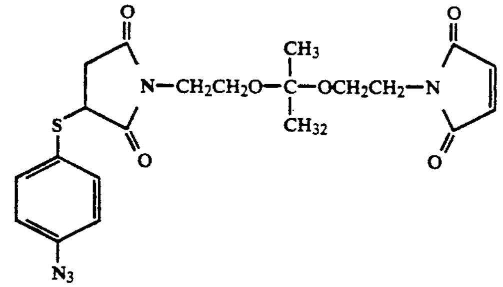

Figure 11:
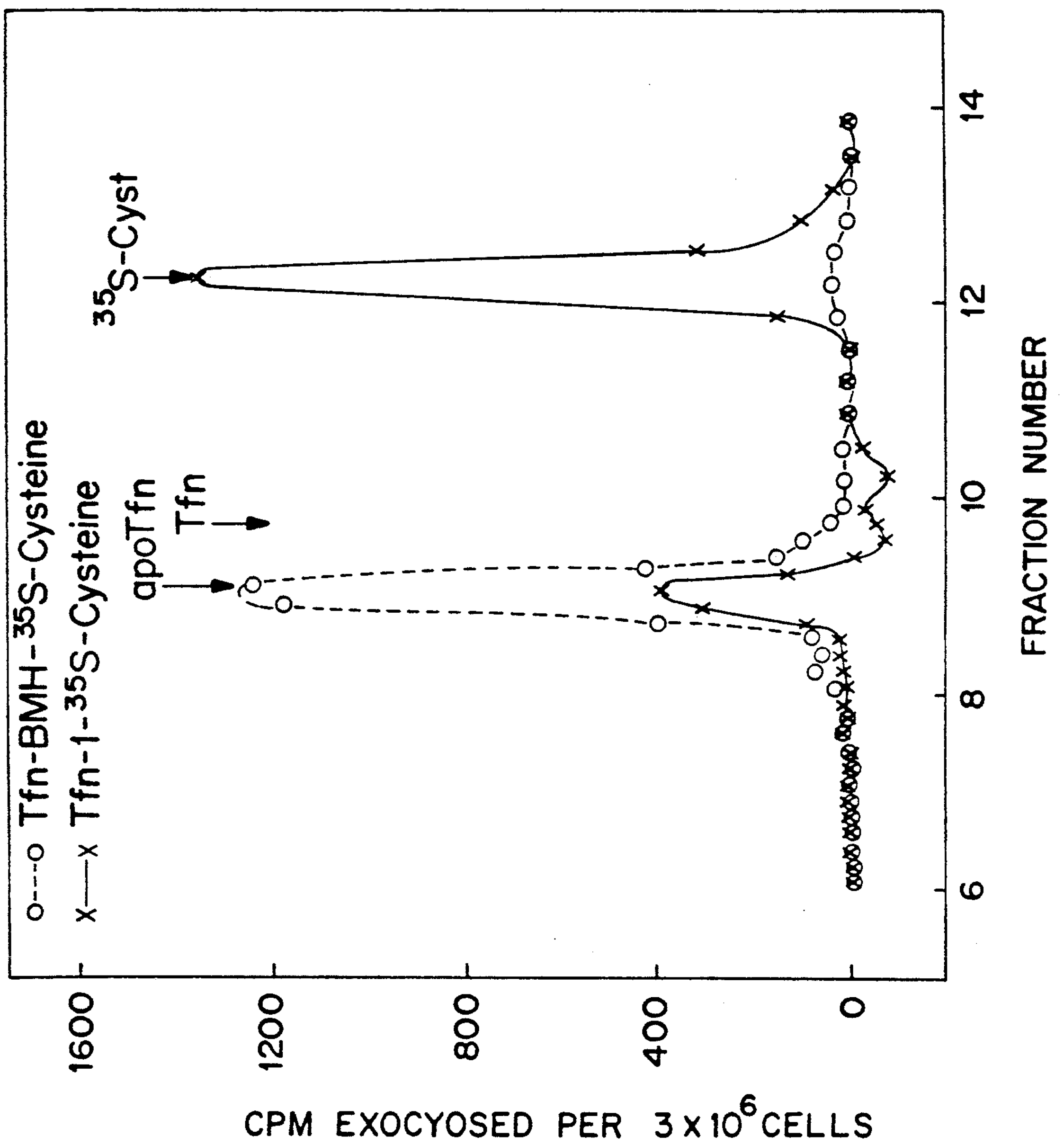
FIG. 11 illustrates the application of crosslinker 1 in reversibly coupling a protein to a matrix.

The acid cleavable crosslinkers of the present invention can be used to reversibly couple proteins to matrices. These immobilized proteins can then be synthetically manipulated with ease, and finally released from the matrix by adjusting the pH. FIG. 11 is a specific illustration of such a use.

Crosslinking of Proteins with Acid Cleavable Reagents

Crosslinking with Cleavable Heterobifunctional Reagents

The reaction conditions for crosslinking with cleavable heterobifunctional reagents are similar to those for use with the non-cleavable linker m-maleimidobenzoyl-N-hydroxysuccinimide ester (MBS) except that the coupling appears to be more efficient with crosslinker 2.

Synthesis of Anti-CD5-diphtheria toxin and Anti-CD5-ricin

CD5 is human T-cell surface membrane epitope which is characteristic of pan T cells. Both toxins, diphtheria toxin (DT) and ricin, are derivatized with crosslinker 2 using 1 mol of crosslinker 2 per mol of toxin dissolved in dry dimethylformamide and added at pH from 8 to 8.5. Unreacted reagent is removed by passage over a small column of G25-F (Pharmacia). The maleimide derivatized toxin is reacted with thiolated antibody (2:1 toxin:antibody) achieved by treatment of 15 mg/ml T101 with 0.6 mM iminothiolane of pH 8.0, for thirty minutes, and subsequent passage over G25-F. Both proteins are allowed to react for twenty minutes. The reactants and products are separated by HPLC chromatography over Zorbax (Z)-250 columns from DuPont run in 90 mM $Na_2SO_4$, 10 mM NaPi (a mixture of mono-and dibasic sodium phosphate), pH 8.5, 1 mM EDTA (90/10/1 buffer, 90 mM $Na_2SO_4$, 10 mM sodium phosphate pH 8.5, 1 mM EDTA). The yields vary between 20 and 50% of input antibody. All thiolations were performed under argon in the presence of 1 mM EDTA to inhibit disulfide bond formation. This procedure can be used to conjugate any IgG monoclonal antibody.

Crosslinking with Acid Cleavable Homobifunctional Reagents

Proteins Which Form Natural Aggregates

Diphtheria toxin dimer was isolated by fractionation of previously frozen diphtheria toxin in 10 mM NaPi of pH 7.1 using a 60×2.5 cm TSK column (LKB). The dimer was thiolated using 1 mM of iminothiolane, pH 8.0, 0.4 M Na borate, for twenty minutes. The dimer was freed from excess iminothiolane and any monomer by Z-250 chromatography and reacted with a seven-fold molar excess of either crosslinker 3 or 4 over the free SH concentration (approximately 1.5 SH/mol diphtheria toxin monomer) for five minutes at pH 8.5. The solution was then diluted ten times with water and made 40% in DMSO to dissociate uncrosslinked species. The crosslinked dimer was isolated by chromatography on a Z-250 column.

The same procedures were used to obtain crosslinked dimers of abrin and crosslinked complexes of asialofetuin and ricin with crosslinker 1.

Proteins Which Do not Form non-covalent Aggregates

Anti-CD5-DT conjugate was crosslinked with crosslinker 1 A nicked DT monomer, 10–15 mg/ml in 0.4 M Na borate, pH 8.0, was derivatized with 0.5–1 mM iminothiolane for thirty minutes, and freed of residual iminothiolane by chromatography on G-25F in pH 8.5 buffer. The derivatized diphtheria toxin was reacted with a 15-fold mol/mol excess of crosslinker 1 dissolved in dry dimethylformamide and after five minutes was rechromatographed on G-25F. The derivatized diphtheria toxin was at that point a mixture of internally crosslinked diphtheria toxin and diphtheria toxin containing one free maleimide group. A 20-fold excess of this diphtheria toxin mixture was then reacted with thiolated T101 as described above at pH 8.5 for thirty minutes. The reactants and products were separated on Z-250 chromatography. The yield of crosslinked conjugate was from about 70 to about 90% by weight, based on input antibody. Mono and bi-toxin conjugates were separated by Z-250 chromatography.

Anti-CD5 ricin linked with crosslinker 1 was prepared by an essentially similar procedure.

For control studies, similar ricin and diphtheria toxin conjugates were crosslinked with the non-cleavable crosslinking reagent bis-maleimidohexane (BMH) by similar methodology. The yields and chromatographic patterns of the non-cleavable products were essentially identical to the cleavable analogs and served as non-cleavable controls.

Hydrolysis of Acid Cleavable Conjugates Resulting in the Release of the Individual Proteins Crosslinked proteins were stored at pH 8.5 in 90/10/1 buffer at 4° C. Acid pulsing was achieved by adding an amount of buffer of higher buffering capacity to achieve the desired lower pH at 25° C. The reaction was stopped by injection into a Zorbax 450 size exclusion HPLC column operated at pH 8 5 in 0.1% SDS. Monomeric and dimeric diphtheria toxin and antibody diphtheria toxin and ricin are all separable by size using a U.V. detector fed to an integrator. The loss of the crosslinked species was quantitated by the appearance of the uncrosslinked species.

Figure 4:
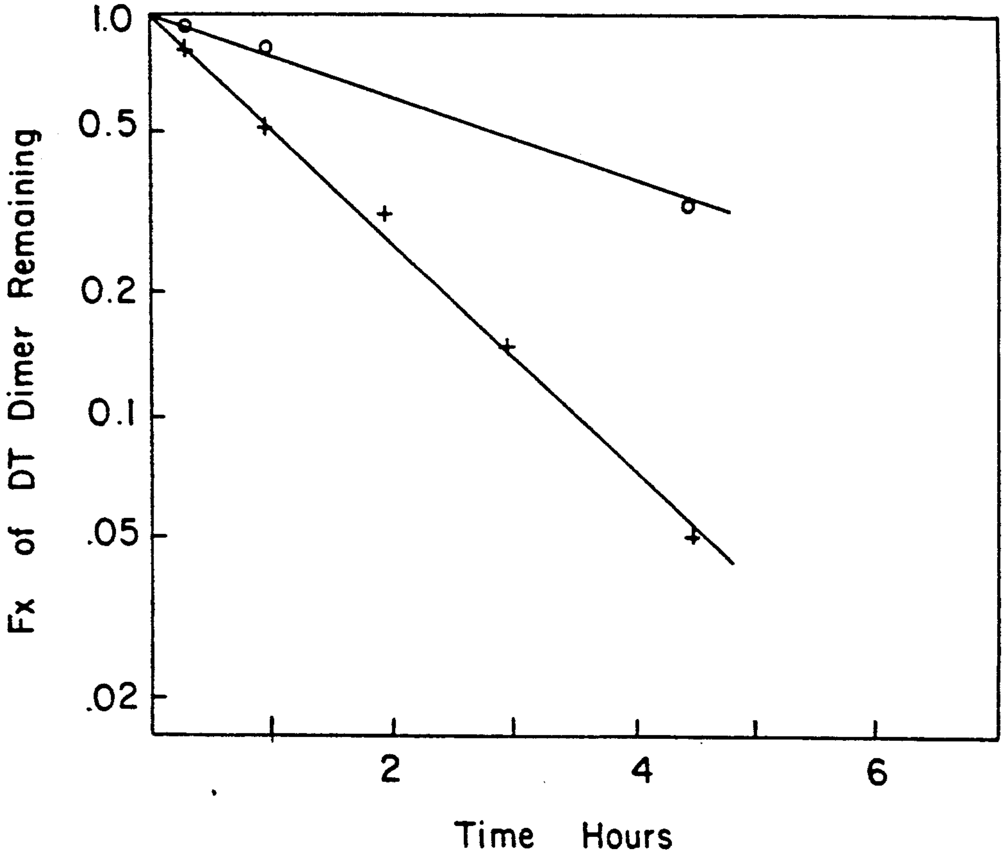
FIG. 4 shows the fractional loss of DT dimers crosslinked with crosslinker 3 (circles) and crosslinker 4 (crosses) as observed with time following acidification to pH 6.4. The loss of dimers is correlated with the appearance of monomers. The reaction kinetics is first order.

Below pH 6.3, acid pulsing of diphtheria toxin was performed in the presence of SDS to prevent precipitation of the diphtheria toxin. FIG. 4 shows the dissociation of crosslinked diphtheria toxin dimers using crosslinkers 3 and 4 into monomers. The log of the fraction of remaining dimer decreases linearly with time, indicating a simple first order process. Acid induced dissociation has also been observed by chromatography in the absence of SDS using 90/10/1 buffer.

The degree of cleavage has been observed down to 0.05 of the crosslinked species and is limited only by the degree of formation of non-cleavable disulfide bonds. The acid induced dissociation of the immunotoxin T101-DT crosslinked with crosslinker 2 is shown in FIG. 5 over a 3 pH unit range. Within experimental error, the observed first order rate constant of dissociation, k, is linearly related to the hydrogen ion concentration. This linear dependence gives the widest possible change in dissociation rates at any two different pH values, and is, a desired feature in a crosslinker which uses a 2 pH unit change (from vascular to acidified vesicle compartment) to achieve a change from a relatively stable state to a labile state. Specific acid catalysis is responsible for the linear dependence of k on $[H^+]$ and is a characteristic of acetal, ketal, and orthoester hydrolysis.

Table I shows a comparison of the half-time of crosslinked protein dissociation determined for four different acid cleavable crosslinkers at 25° C. Between 25° C. and 37° C., hydrolytic rates change by less than two-fold. The pH stability of the series is acetal>ketal>orthoester, and is in general agreement with the literature of the parent compounds. These crosslinkers were synthesized to cover a wide range of hydrolytic rates. Major variables promoting acid liability include stabilization of the carbonium ion intermediate by electron donating groups and increasing acidity of the parent alcohol.

TABLE I

| | Comparison of Crosslinked Protein Dissociation Half-lives at pH 5.5 | | | |
|---|---|---|---|---|
| Cross-linker | Type | Acid Cleavable Group | Reactive Groups | $T_{\frac{1}{2}}$ pH 5.5 hours |
| 4 | Homobifunctional | Orthoester | bis maleimide | 0.1 |
| 3 | Homobifunctional | Orthoester | bis maleimide | 0.3 |
| 1 | Homobifunctional | Ketal | bis maleimide | 0.7 |
| 2 | Hetero-bifunctional | Acetal | maleimide, NHS ester | 139. |

half-lives determined at pH 6.5 ± 0.1 for 4, and 3, and extrapolated to pH 5.5 assuming a linear dependence of $k_{dis}$ on $[H^+]$. All measurements at 25°

Blocking and Unblocking of a Protein Toxin Functional Domain with the Aid of an Acid Cleavable Crosslinker Cold induced dimerization of diphtheria toxin has been shown to result in a functional loss of the diphtheria toxin binding domain and a corresponding loss of toxicity (Carroll et al., *Biochemistry* 25:2425-2430, 1986). Treatment of dimers with DMSO converts dimers to monomers (unnicked) and restores binding and toxicity.

Figure 6:
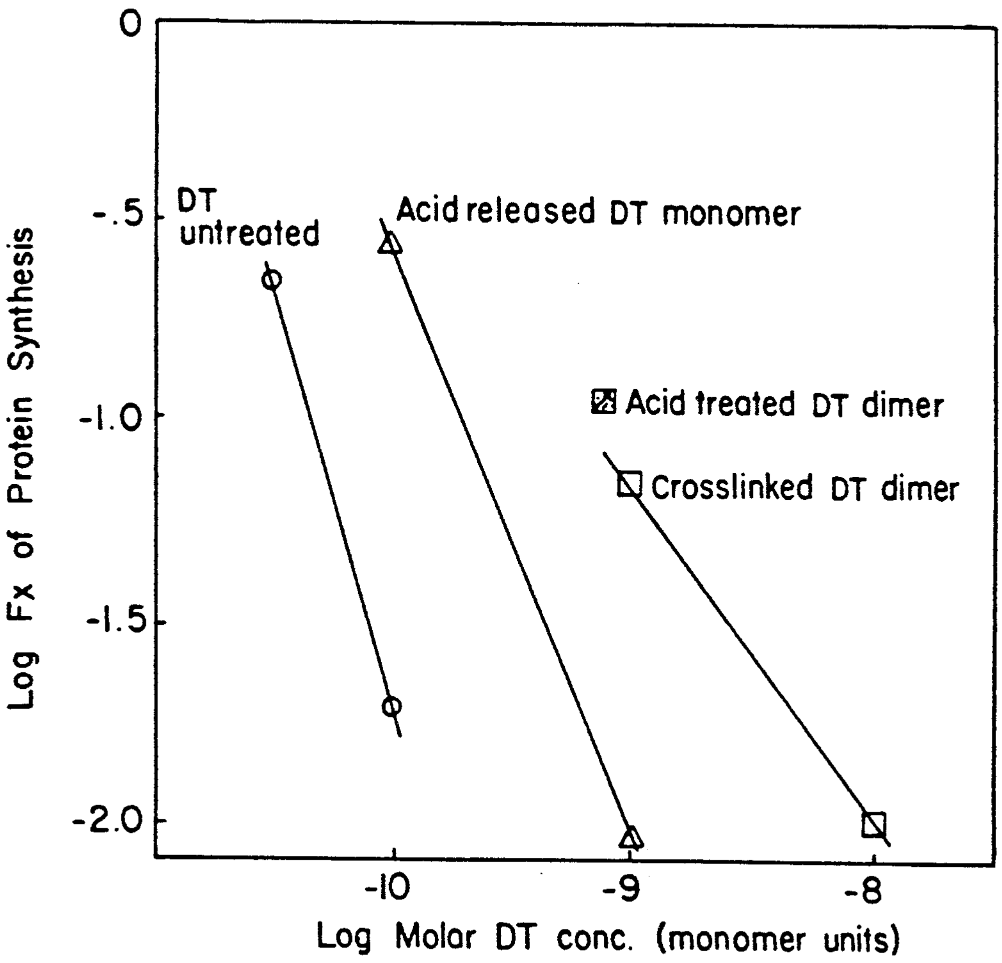
FIG. 6 shows that the increasing concentration of DT progressively inhibits the protein synthesis of Vero cells. Dimers crosslinked by crosslinker 3 are less toxic, requiring 30-fold higher concentrations for equal inhibition. Treatment at pH 6.5 of the crosslinked dimer for two hours converts about half the dimer into monomer with partial restoration of the original toxicity.

Unnicked diphtheria toxin dimer was isolated and crosslinked with crosslinker 3, forming a covalently stable dimer which could not be dissociated with 40% DMSO. Over 90% of the crosslinked dimer toxicity was lost as assayed by inhibition of protein synthesis on Vero cells following a thirty minute incubation, wash, and reincubation for 2.5 hours, as shown in FIG. 6. The dimer was acid pulsed from pH 8.5 to pH 6.5 for two hours and chromatographed in 90/10/1 buffer on Z-250. Approximately ½ of the dimer peak was converted to monomer. Both peaks were isolated. The dimer peak toxicity was unchanged, while the monomer peak toxicity was increased. The unnicked diphtheria toxin derivatization with iminothiolane accounts for a 0.5 log loss of diphtheria toxin toxicity over untreated unnicked diphtheria toxin monomer.

Figure 7:
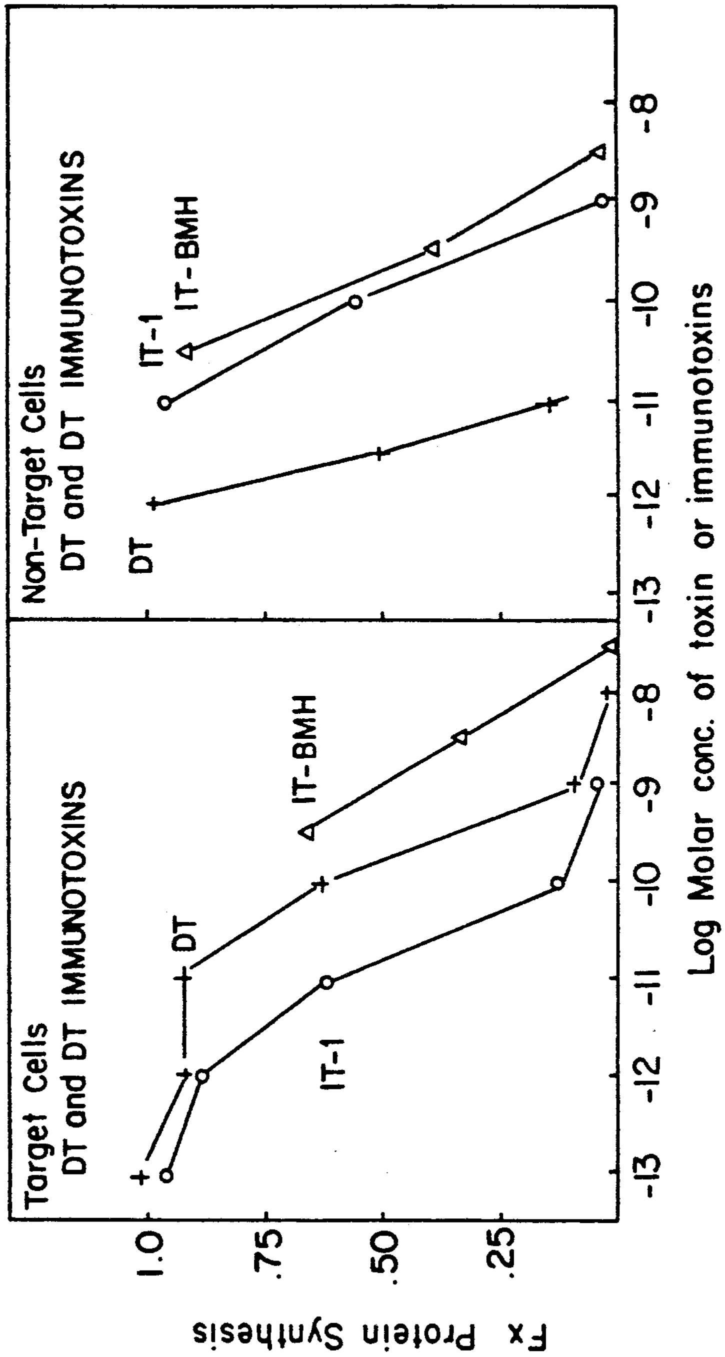
FIG. 7 shows the potency of DT and T101 (Anti-CD5) conjugates of DT, assayed by protein synthesis inhibition, made with the non-cleavable crosslinker BMH and the cleavable ketal crosslinker 1, compared on non-target (Vero) cells (panel b, right) lacking CD5 surface antigen and target (Jurkat) cells (panel a, left) carrying CD5. The ketal linked conjugate is 50-fold more potent than the BMH conjugate on target cells. Jurkat assay, 6 hours at 37° C.
Figure 8:
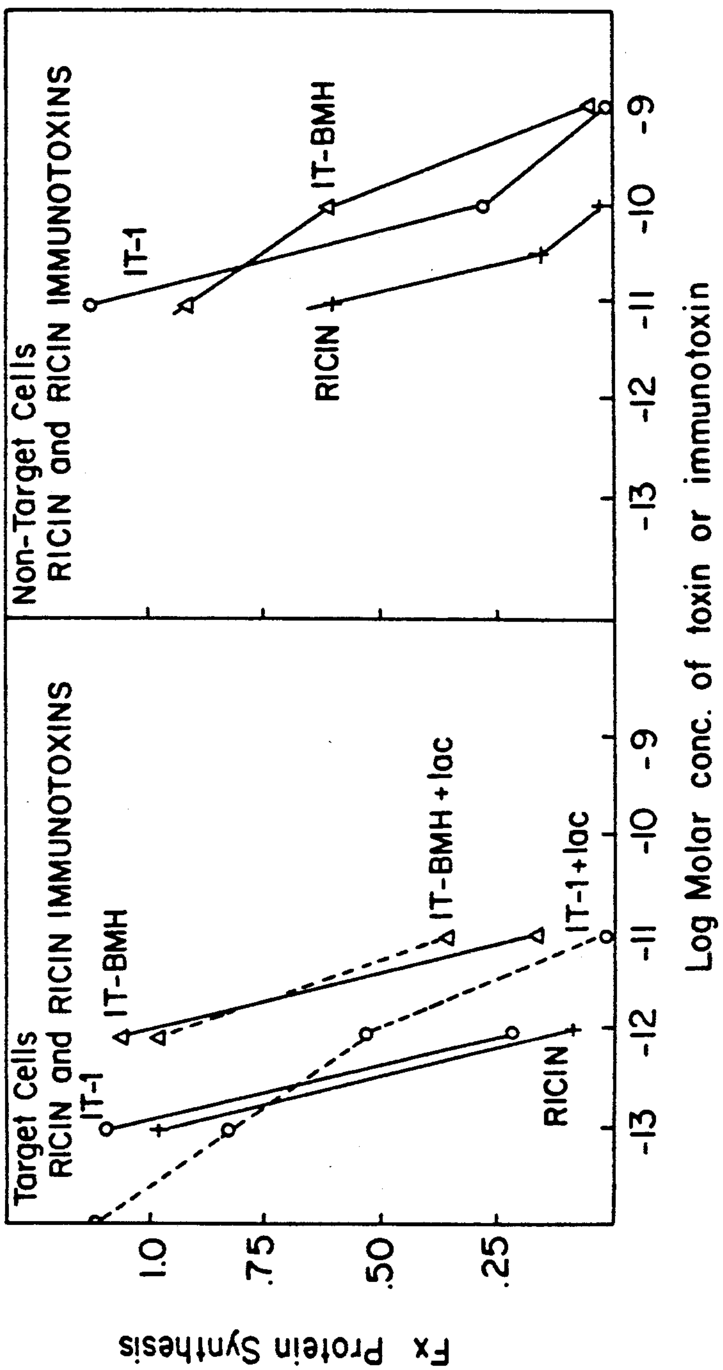
FIG. 8 shows the potency of ricin and T101 (Anti-CD5) conjugates of ricin assayed by protein synthesis inhibition made with the non-cleavable crosslinker BMH and the cleavable ketal crosslinker 1, compared on non-target (Vero) cells (panel b, right) lacking CD5 surface antigen and target (Jurkat) cells (panel a, left) carrying CD5. The ketal linked conjugate is 10-fold more potent on the target cells. The dashed lines are plus 100 mM lactose.

Enhanced toxicity of Immunotoxins Constructed with Ketal Based Cleavable Crosslinker The potency of Anti-CD5 immunotoxins constructed with the cleavable crosslinker 1 is enhanced toward Jurkat target cells over the non-cleavable crosslinker BMH. The potency increase is 1.75 logs or 50-fold for the diphtheria based immunotoxin and 1 log for the ricin based immunotoxin as shown in FIGS. 7*a* and 8*a*, respectively. The 50-fold enhancement for the diphtheria toxin conjugate is almost entirely specific for the antibody route, not being seen on the non-target Vero cells (cf. FIG. 7*b*).

It is noted in FIG. 7*b* that upon conjugation with antibody using BMH, the diphtheria toxin potency is reduced 50-fold. Steric effects due to antibody conjugation could act to reduce toxicity at several steps along the intoxication pathway, including:

1) inhibition of binding to diphtheria toxin receptor;

2) inhibition of membrane translocation to the cytosol;

3) inhibition of diphtheria toxin receptor-mediated uptake to the compartment productive of toxicity; and 4) various combinations of the above It is expected that a cleavable conjugate would regain a potency loss caused by antibody induced steric inhibition of translocation. The gain in potency should occur on both target and non-target cells Alternatively, a potency loss on non-target cells due to antibody induced steric constraints of diphtheria toxin binding should not be overcome by intracellular cleavage. Additionally, no increase in potency on target cells would be expected if the entry route is largely antibody mediated, as is demonstrated by a 1 and 2.5 log shift to higher concentrations by excess antibody for the bis-maleimidohexane (BMH) and the cleavable conjugate, respectively. The cleavable conjugate does not restore toxicity to non-target cells. However, when the entry route is via the antibody on the target cells, the lost potency of the BMH conjugate is fully recovered by cleavable conjugate. This suggests either that the diphtheria toxin receptor-mediated inhibited, or that there were various combinations of the above possibilities. When the uptake is via the antibody route, access to the compartment product of diphtheria toxin toxicity is apparently enhanced by cleavage of the antibody moiety. For the ricin conjugate, half of the 10-fold loss in potency with the BMH conjugate is recovered on non-target cells and the full 10-fold amount is recovered on target cells with crosslinker 1, indicating that a combination of steric factors are operating with this conjugate.

The choice of BMH as a non-cleavable control crosslinker was dictated by its similar structure to crosslinker 3. BMH has six flexible methylene groups separating the bis-maleimide moieties. Crosslinker 3 has seven residues (five methylene, two oxygen) in this position, and is somewhat less flexible due to the 120° oxygen bond angles and steric hindrance from the ketal methyl groups. BMH is the most flexible commercially available maleimide crosslinker. It has been noted that crosslinkers having less flexibility than BMH, such as m-maleimidobenzoyl-N-hydroxysuccinimide ester and succinimidyl 4-(p-maleimidophenyl)butyrate induce larger losses in toxicity of ricin and diphtheria toxin when conjugated to T101 as compared to BMH assayed on non-target cells.

Because of the high sensitivity of Jurkat cells to ricin, the ricin conjugate is partially inhibited by lactose. The entire toxicity is not being mediated by the antibody route. The diphtheria toxin conjugate is largely mediated by the antibody route since 100-fold excess of T101 shifts the dose response curve by 2.5 logs to higher conjugate concentrations.

Reversible Steric Inhibition of Toxin Receptors and Binding Domains by Polyethylene Glycol Conjugation via an Acid Cleavable Crosslinker Mono methoxy polyethylene glycol of average molecular weight 5000 can be activated with acylating groups capable of coupling to amino groups such as NHS esters (Polysciences); phenyl-chloroformate (Veronese et al. *App. Biochem. Biotechnol* 11: 141-152, 1985) or 1,1'-carbonyldimidazole (Beauchamp et al., *Anal. Biochem.* 131: 25-33,, 1983). Activated polyethylene glycol was reacted with a twenty-fold molar excess of cysteamine.2HCl at pH 8.5. The derivatized disulfide was then reduced with 50 mM dithiothreitol and the polyethylene glycol-SH derivative was freed of excess reactants by size exclusion chromatography. The polyethylene glycol-SH was reacted with a fifteen-fold excess of crosslinker 1 at pH 8.0. The maleimide derivative was freed of excess reactant by size exclusion chromatography and was immediately reacted with thiolated ricin or thiolated diphtheria toxin derivatized with iminothiolane to provide 4SH groups/mol of toxin. Coupling of the polyethylene glycol-toxin to antibody is performed as described above or via polyethylene glycol containing two maleimide residues by using polyethylene glycol containing from two to four OH groups and proceeding as above. Increased steric blockade can be provided by using higher molecular weight polyethylene glycol fractions such as PEG 20.

Multiple polyethylene glycol molecules have been coupled to diphtheria toxin via crosslinker 1. Steric inhibition of toxicity to non-target cells has been achieved (2.5 logs). Studies of hydrolytic rates of release of free diphtheria toxin between pH 5.5 and 6.5 indicate that the dependency on [H+] is to a power greater than 1.

A Direct Demonstration that a Protein Conjugate Made with Crosslinker 1 is Hydrolyzed within the Endosomal Compartment Following Receptor-mediated Endocytosis The iron transporting protein diferric transferrin, Tfn, has been shown to undergo the following cyclic steps:

1) cell surface receptor binding;
2) receptor-mediated endocytosis;
3) acid promoted release of iron within the endosome following endosomal acidification;
4) exocytosis of receptor bound apotransferrin;
5) dissociation of apotransferrin to the medium.

(Klausner et al., JBC 258: 4715-4724, 1983; Ciechanover et al., JBC 258: 9681-9689, 1983). The average transit time for steps 2-5 is about 15 minutes.

The complex Tfn-S-[mal-x-mal]$^{35}$S-cysteine where [mal-x-mal]represents crosslinker 1 was synthesized. Tfn was thiolated with iminothiolane, reacted with an excess of crosslinker I, and then reacted with $^{35}$S-radiolabelled cysteine. A similar non-cleavable conjugate was constructed with BMH. The conjugates consisted largely of Tfn, but contained some apoTfn. At approximately 77 nM, specific binding and uptake by $3\times10^6$ K562 cells was 5.7% and 4.8% of the input tracers ($2\times10^5$CPM) after thirty minutes exposure for crosslinker 1 and BMH conjugates, respectively.

Following a loading period as described above conducted in the presence and absence of energy inhibitors (50 MM deoxyglucose and 10 mM Na azide), the cells were washed, and fresh medium plus and minus energy inhibitors was added containing 30 microg/ml cold Tfn. The cells were reincubated for thirty minutes at 37° C. The supernatants were harvested, made up to 0.5% in SDS and chromatographed by size exclusion on Z-450 column in 0.1% SDS in 0.1 M NaPi, (a mixture of mono- and dibasic sodium phosphate) pH 8.5, 1 mM EDTA. This chromatographic procedure separates Tfn from apoTfn and both from free $^{35}$S-cysteine-S-maleimide alcohol, the low molecular weight hydrolysis product of the crosslinker 1 conjugate.

The energy inhibitors stop the cycling of Tfn after one cycle, so that supernatants from energy inhibited cells contain Tfn and apoTfn loaded into the cell and released from the surface membrane after at most one cycle through the cell. The supernatant from the non-inhibited cells contains apoTfn loaded during the entire first incubation and exocytosed during the second incubation, as well as the membrane bound contribution. By subtracting the values of the inhibited cells from the non-inhibited cell, one eliminates the membrane bound contribution and obtains the contribution of material which has undergone cycling through the endosome compartment of these cells.

Figure 10:
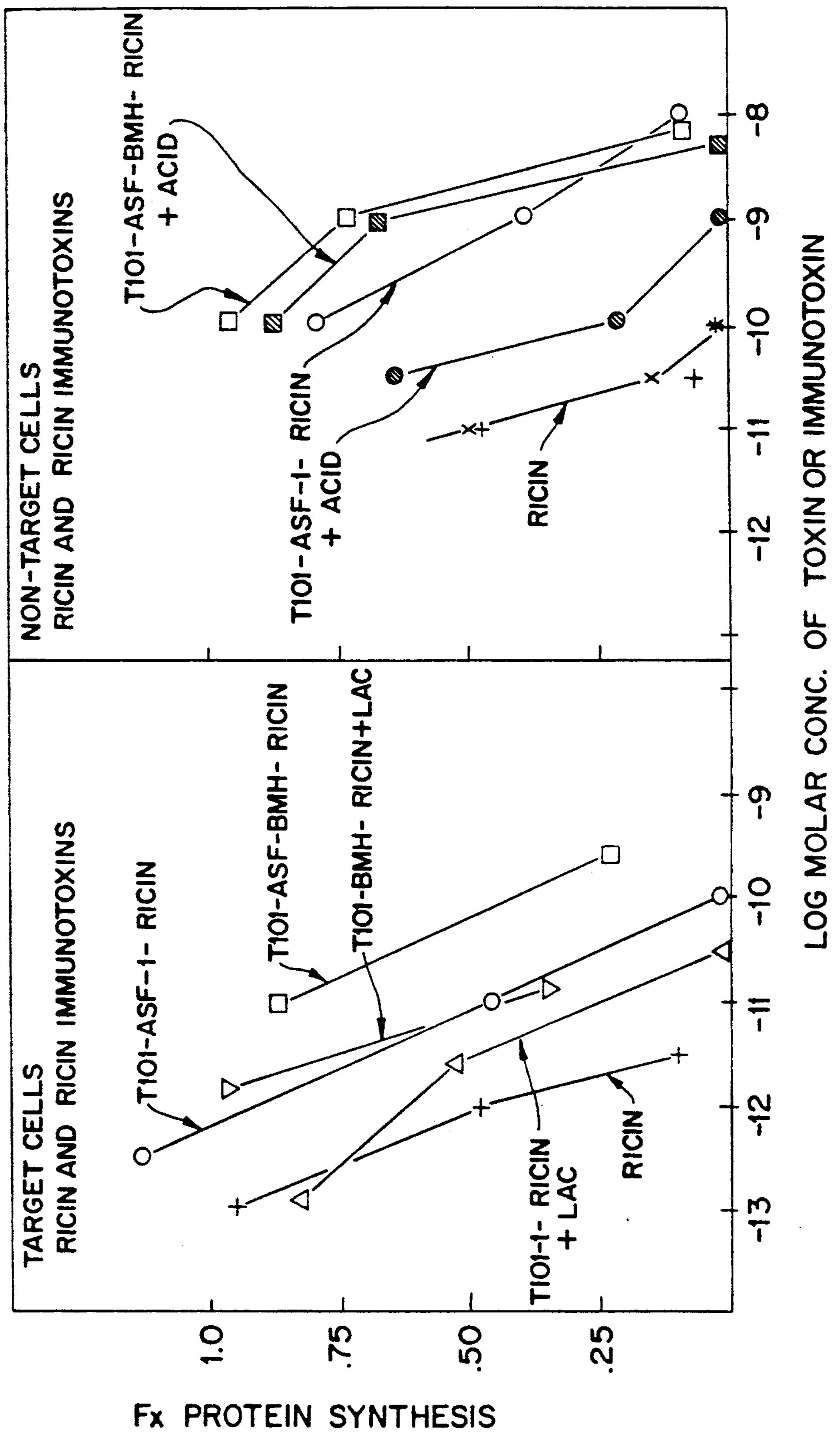
FIG. 10 shows intracellular hydrolysis of 35S-cysteine from the conjugate transferrin-crosslinker 1.

FIG. 10 graphs the $^{35}$S-cysteine counts versus the retention time on the column for both conjugates from the second incubation supernatants. The non-cleavable conjugate appears at the retention time of apoTfn, indicating that it has cycled through the cell and lost its iron. Less than 3% of the counts have been liberated by hydrolysis. In contrast, the conjugate constructed with crosslinker 1 has lost 65% of its $^{35}$S-cysteine to a fraction eluting coincident with free $^{35}$S-cysteine (The column cannot resolve $^{35}$S-cysteine from the $^{35}$S-cysteine-maleimide alcohol hydrolytic product). The hydrolytic product has been largely exocytosed to the medium, unlike the liberated iron. This presumably reflects the lack of an accepter or receptor for the low molecular weight hydrolytic product in contrast to iron. Because the half-time of hydrolysis of this cleavable conjugate at pH 5.5 is roughly equal to the Tfn transit time (within a factor of 2), an appreciable fraction, 0.35, remains non-hydrolyzed.

Figure 9:
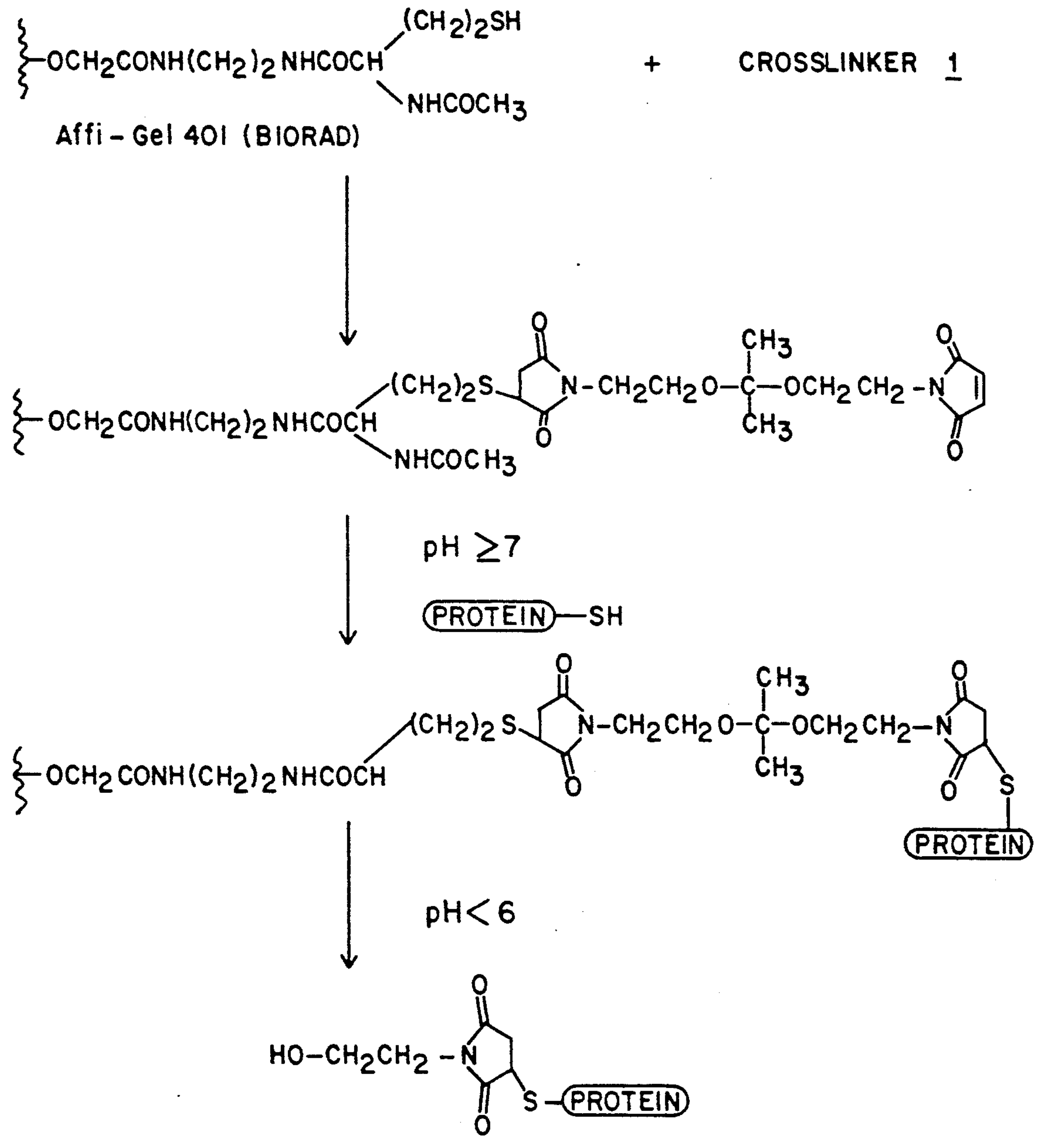
FIG. 9 shows a comparison of the ricin binding site of an Anti-CD5 (T101) immunotoxin reversibly blocked by the inclusion of asialofetuin linked to ricin via crosslinker; 1 A similar but non-reversibly blocked immunotoxin was constructed with BMH.

In FIG. 9, the ricin binding site of an Anti-CD5 (T101) immunotoxin has been reversibly blocked by the inclusion of asialofetuin linked to ricin via crosslinker 1 A similar but non-reversibly blocked immunotoxin was constructed with BMH. On target cells, the reversibly blocked conjugate is 1 log more potent than the BMH conjugate. On non-target cells, toxicity of both are 2 logs less than ricin. On acid treatment, ricin toxicity is regained within 0.5 log of the original toxicity.

In FIG. 10, the intracellular hydrolysis of $^{35}$S-cysteine from the conjugate transferrin-crosslinker 1 $^{35}$S-cysteine is observed after following a 30 minute loading into K562 cells ($2\times10^5$CPM) and a 320 minute exocytosis period into fresh medium. The arrows indicate the elution times of apotransferrin, diferric transferrin, and cysteine on the Z-450 column run in SDS. The graphed counts are the difference between the supernatant without energy inhibitors minus the supernatant with energy inhibitors.

Coupling of multiple (2-4) molecules to diphtheria toxin via crosslinker 1 has been performed. Steric inhibition of toxicity to non-target cells has also been achieved (2.5 logs).

According to the present invention, proteins or toxins can be sterically inhibited by using the acid cleavable crosslinkers of the present invention, so that the

[H+]dependence is increased by a power greater than 1. Delays of hydrolysis of the conjugate are achieved at early times at higher vascular pH values. This widens the therapeutic ratio of an immunotoxin or reversibly blocked macromolecular prodrug.

The present invention is an improvement over the use of lactose to block the ricin binding outside the cell, as the ricin binding site is reversibly blocked by crosslinking with a non-covalent complex of ricin and asialofetuin (ASF). These complexes associate via the galactose residues on ASF and the ricin galactose binding site. Ricin and ASF are thiolated with 5 mM IT as previously described. m-Maleimidobenzoyl-N-hydroxysuccinimide ester (MBS) is added to T101, providing one derivatized maleimide per molecule of T101. ASF is added at the rate of one mol per mol of T101. The T101-ASF complex is isolated by chromatography on Z-250.

Thiolated ricin is added to the T101-ASF complex at 1 mol per mol of antibody in the presence of borate buffer to reduce aggregation. Crosslinker 1 is added in excess, and crosslinks the remaining SH groups on the ASF to the ricin SH groups. The T101-ASF-ricin complex is purified by chromatography on Z-250 in 90:10:1 buffer plus 100 mM lactose (used to dissociate non-crosslinked ricin). The successful blockade of ricin galactose binding sites is demonstrated by the fact that the complex is not bound or retarded by affinity chromatography over an ASF-sepharose column, in contrast to free ricin or T101-ricin.

For in vivo use, the exposed asialo-galactose groups on the ASF moiety of T101-ASF ricin are sialated using CMP:NANA-Galbeta (1,4)GlcNAC-alpha-2,6-sialyltransferase (Genzyme Corp.) according to the supplier's instructions, except that the reaction pH is raised to pH 8.0. This is done to prevent hepatic uptake of the immunotoxin via the hepatic asialoglycoprotein receptor.

FIG. 9, Panel B, shows that the T101-ASF-Ricin complex has a 100-fold reduction in toxicity (ricin route) on non-target cells. Acid treatment releases most of the ricin as judged by the 50-fold increase in toxicity. This fact was verified by HPLC. In panel A of FIG. 9, the toxicity of T101-Ricin crosslinked with crosslinker 1 in the presence of 100 mM lactose (normalized to ricin toxicity) is compared to the T101-ASF-Ricin without lactose. The ASF blocked ricin immunotoxin compares favorably with the immunotoxin utilizing lactose blockade. The toxicity of the ASF blocked immunotoxin is largely via the T101 route, as demonstrated by the loss of toxicity achieved by adding excess competing T101 (data not shown).

The data of FIG. 9 demonstrate that a functional ricin binding site is required within an intracellular compartment for full efficacy of the T101-ASF-ricin immunotoxin. This is demonstrated by the reduced efficacy of the immunotoxin made with the non-cleavable (BMH) crosslinker which lacks the functional binding site. The blocked ricin binding site may thus be unblocked within the cell by using a crosslinker which is cleavable by an intracellular component, in this case, dilute acid.

As can be seen from the above, the data validate the concept of reversible blockade of a toxin binding site in an immunotoxin to achieve enhanced efficacy while maintaining target cell specificity. This concept can be applied to immunotoxins constructed with a wide variety of toxins, monoclonal antibodies, and other targeting ligands. Although a small class of targeting ligands which are rapidly internalized such as transferrin and Anti-CD3 monoclonal antibodies and other targeting moieties operating on receptors in very high numbers (over $0.5\times10^6$ per cell) may not require the toxin binding site for full immunotoxin efficiency, as disclosed by Greenfield et al. (1987) Science 238: 635-639, but in general, most monoclonal antibody toxin-conjugates require this feature for full efficacy.

Thus, the conjugates of the present invention can be effectively used to kill unwanted cell types in vivo and in vitro.

According to the present invention, the cellular component causing cleavage is not appreciably present in the serum, the cellular component is present within a compartment to which the immunotoxin is routed by the targeting moiety, and the intracellular cleavage is sufficiently rapid to restore substantially full activity in which any cleavage rate in serum rate is at least 0.01 fold lower and preferably more.

Other examples of conjugates according to the present invention are linkages consisting of peptide bonds or glycoside units which are cleavable by either intracellular cathepsins or glycosidases present in internal vesicles and Golgi compartments, respectively. These linkages are to be used in conjunction with agents which hinder toxin binding sites, such as ASF or glycopeptides for ricin, and polyethylene glycol for a variety of toxins as already described herein.

The conjugates of the present invention are particularly useful in treating AIDS, or acquired immune deficiency syndrome. These anti-human pan T cell conjugates break the infectious cycle of AIDS by killing the major cell types harboring HIV, T cells, and macrophages. For the T101-ASF-ricin immunotoxin, T cells are killed via the anti-CD5 moiety, and macrophages are killed via the ricin mannose residues which have high affinity for macrophages (cf. *Cell* 19: 207-215, 1980). Administration of the conjugates is preferably intraperitoneally or intravenously. Optimal dosages are a single administration of about 10 to about 100 micrograms of ricin moiety/kg body weight.

The anti-CD5 moiety was chosen because the subset of T cell harboring virus, CD4, is embraced by CD5. However, CD4 antigen density is known to substantially diminish following infection and viral replication, making this epitope unsatisfactory for targeting purposes. This therapy may be performed in the presence of agents which inhibit viral replication.

Anti-CD5 immunotoxins made with mutant diphtheria toxins which are blocked in binding but not in translocation, such as CRM 107 and CRM 103, or truncated toxin mutants, or chemically altered toxin having similar properties, are also useful in AIDS therapy as described above, except that these immunotoxins lack macrophage and monocyte killing ability. These functions must be provided by utilizing an immunotoxin mixture specific for all of the needed epitopes as was done in U.S. Pat. No. 4,520,226, which patent is incorporated herein by reference. The improvement herein is that each immunotoxin is constructed with a cleavable crosslinker, providing increased efficacy.

The dosage of CRM 107 based immunotoxins ranges from about 300 to about 300 micrograms/kg of body weight in terms of mutant diphtheria weight content, and from CRM 103 based conjugates, from about 3 to about 30 micrograms/kg of body weight, administered one time only.

The crosslinked conjugates of the present invention may be used to prepare prodrugs, which can be used to deliver an amino-group-containing biologically active substance to selected members of a heterogeneous population of cells by exposing the cells to a complex formed by crosslinking the active substance to a cell-binding partner specific for a cell-surface receptor of the selected cells. The compound binds selectively to those cells, and the active substance is released from the complex by exposure to a pH sufficiently low to cleave the crosslinker bond between the active substance and the crosslinker.

The conjugates of the present invention may be administered to a patient in a variety of forms, although intravenous or intraperitoneal administration of the active ingredient in a suitable pharmaceutically acceptable vehicle is the preferred delivery route.

Compositions within the scope of the present invention include compositions wherein the active ingredient thereof is contained in an effective amount to achieve its intended purpose. Determination of the effective amounts, of course, is well within the skill in the art.

In addition to the conjugates of the present invention, the pharmaceutical compositions of the present invention may contain any suitable pharmaceutically acceptable carriers comprising excipients and auxiliaries which facilitate processing of the conjugates into preparations which can conveniently be used pharmaceutically.

Suitable formulations for parenteral administration include aqueous solutions of the conjugates in water-soluble form. In addition, suspensions of the conjugates as appropriate oily injection suspensions may also be administered. Suitable lipophilic solvents or vehicles include fatty oils, for example, sesame oil, or synthetic fatty acid esters, such as ethyl oleate or triglycerides. Aqueous injection suspensions may contain substances which increase the viscosity of the suspension such as sodium carboxymethyl cellulose, sorbitol, and/or dextran. Optionally, the suspension may also contain stabilizers.

The heterobifunctional crosslinkers are superior to the homobifunctional crosslinkers for linking two different molecules. However, the heterobifunctional crosslinkers are more difficult to synthesize.

While the invention is described above in relation to certain specific embodiments, it will be understood that many variations are possible, and that alternative materials and reagents can be used without departing from the invention. In some cases such variations and substitutions may require some experimentation, but such will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A conjugate comprising a biologically active component for inhibiting or killing unwanted cells crosslinked with a crosslinker to a targeting moiety comprising a binding partner to cell surface features wherein the crosslinker can be cleaved under mild acidic conditions and wherein the crosslinker is formed from a compound selected from the group consisting of compounds of the following formulas:

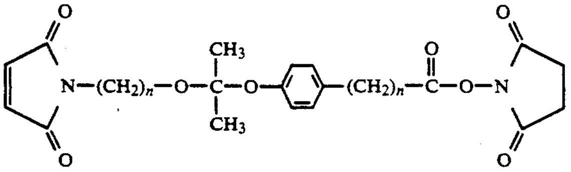

wherein n is at least 1;

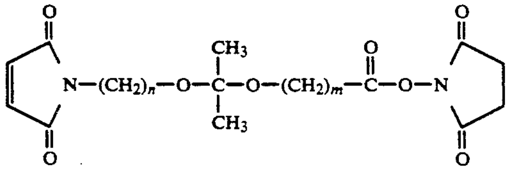

wherein n is at least 1 and m is at least 1;

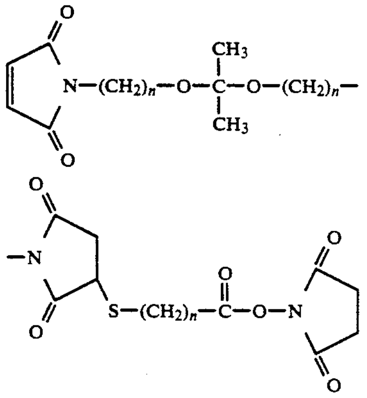

wherein n is at least 1;

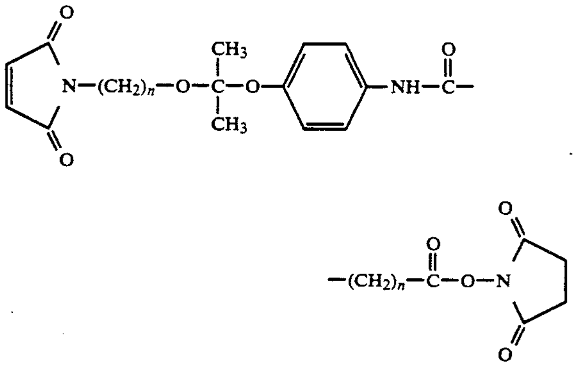

wherein n is at least 1;

wherein n is at least 1;

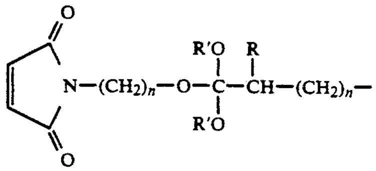

-continued

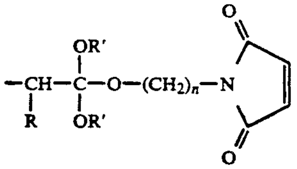

wherein n is at least 1, R' is selected from the group consisting of $C_1$ to $C_8$ alkyl groups and R is selected from the group consisting of H and $C_1$ to $C_8$ alkyl groups; and

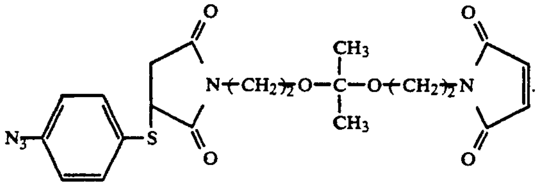

2. The conjugate of claim 1, wherein the crosslinker is formed from the compound of the formula:

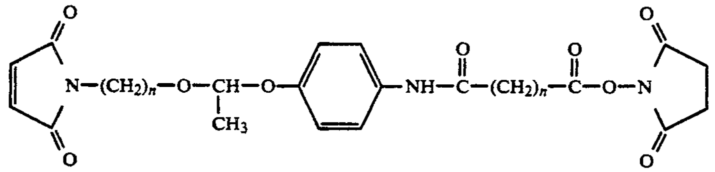

wherein n is 2.

3. The conjugate of claim 1, wherein the crosslinker is formed from the compound of the formula:

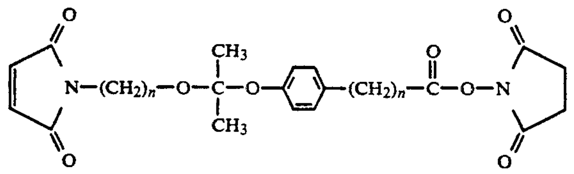

wherein n is 2.

4. The conjugate of claim 1, wherein the crosslinker is formed from the compound of the formula:

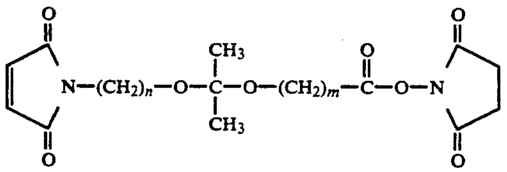

wherein n and m are each 2.

5. The conjugate of claim 1, wherein the crosslinker is formed from a compound of the formula:

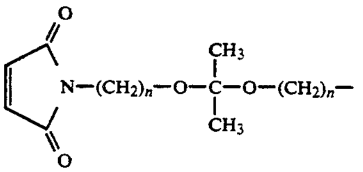

-continued

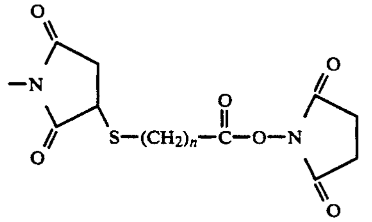

wherein n is 2.

6. The conjugate of claim 1, wherein the targeting moiety is an antibody.

7. The conjugate of claim 1, wherein the biologically active component is a cell toxin.

8. The conjugate of claim 1, wherein the biologically active component is a ribosomal-inactivating protein.

9. The conjugate of claim 8, wherein the biologically active component is selected from the group consisting of ricin, diphtheria toxin, diphtheria toxin mutants, abrin, melphalan, bleomycin, adriamycin, and daunomycin.

10. The conjugate of claim 6, wherein the antibody is a monoclonal antibody.

11. The conjugate of claim 1, wherein the biologically active component is selected from the group consisting of proteins, peptides, and nucleic acids.

12. The conjugate of claim 11, wherein the protein is an enzyme.

13. The conjugate of claim 1, wherein the biologically active component is a drug.

14. The conjugate of claim 1, wherein the targeting moiety is selected from the group consisting of antibodies, cell membrane transport agents and protein hormones.

15. A pharmaceutical composition comprising:

a conjugate of a biologically active component crosslinked with a crosslinker to a targeting moiety comprising a binding partner to cell surface features wherein the crosslinker can be cleaved under mild acidic conditions and wherein the crosslinker is formed from a compound selected from the group consisting of compounds of the following formulas:

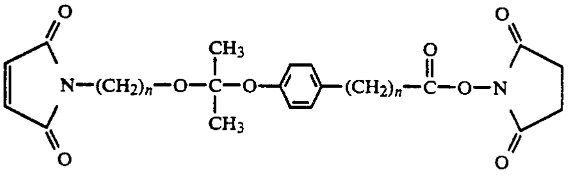

wherein n is at least 1;

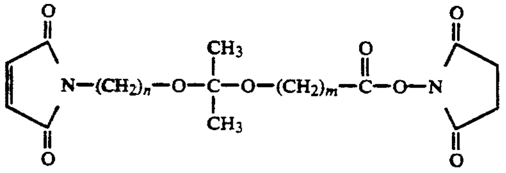

wherein n is at least 1 and m is at least 1;

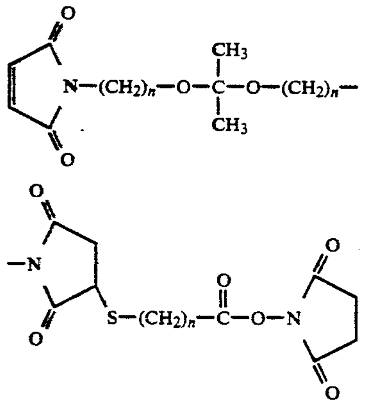

wherein n is at least 1;

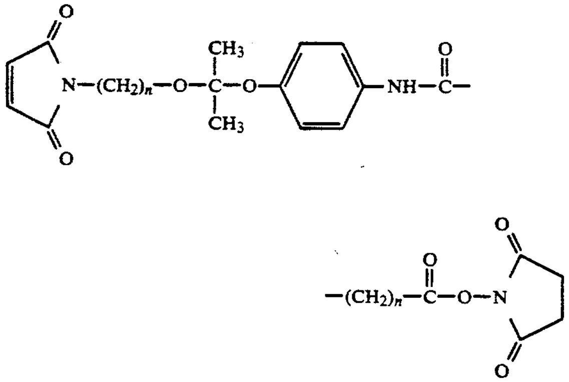

wherein n is at least 1;

wherein n is at least 1;

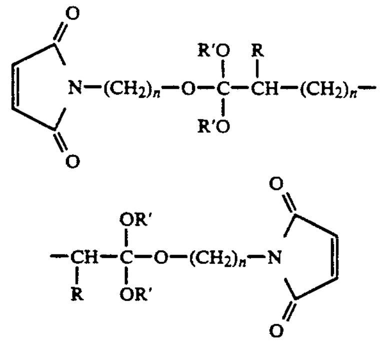

wherein n is at least 1, R' is selected from the group consisting of $C_1$ to $C_8$ alkyl groups and R is selected from the group consisting of H and $C_1$ to $C_8$ alkyl groups;

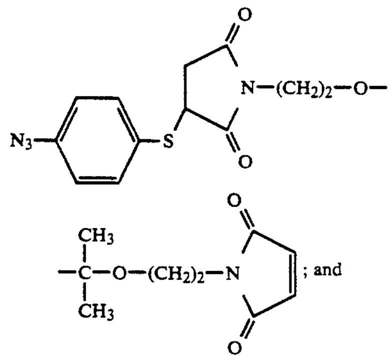

; and a pharmaceutically acceptable carrier.

16. The composition of claim 15, wherein the carrier is an isotonic solution.

17. The composition of claim 15, wherein the targeting moiety is an antibody.

18. The composition of claim 15, wherein the biologically active component is selected from the group consisting of proteins, peptides, and nucleic acids.

19. The composition of claim 18, wherein the protein is an enzyme.

20. The composition of claim 15, wherein the biologically active component is a drug.

21. The composition of claim 15, wherein the targeting moiety is selected from the group consisting of antibodies, cell membrane transport agents and protein hormones.

* * * * *